United States Patent
Le Claire et al.

(10) Patent No.: US 11,007,134 B1
(45) Date of Patent: May 18, 2021

(54) CERAMIDE CONTAINING CAPSULES, CERAMIDE COMPOSITIONS, AND COSMETIC COMPOSITIONS THEREOF

(71) Applicant: L'OREAL, Paris (FR)

(72) Inventors: Laurianne Le Claire, Eaubonne (FR); Miao Wang, Westfield, NJ (US); Jerome Cottard, Dammartin en Goële (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/835,930

(22) Filed: Mar. 31, 2020

(51) Int. Cl.
*A61K 8/68* (2006.01)
*A61K 8/11* (2006.01)
*A61K 8/90* (2006.01)
*A61K 8/85* (2006.01)
*A61K 8/35* (2006.01)
*A61Q 19/00* (2006.01)
*A61K 8/55* (2006.01)

(52) U.S. Cl.
CPC ............... *A61K 8/68* (2013.01); *A61K 8/11* (2013.01); *A61K 8/35* (2013.01); *A61K 8/553* (2013.01); *A61K 8/85* (2013.01); *A61K 8/90* (2013.01); *A61Q 19/00* (2013.01); *A61K 2800/30* (2013.01); *A61K 2800/624* (2013.01); *A61K 2800/652* (2013.01)

(58) Field of Classification Search
CPC ... A61K 8/68; A61K 8/11; A61K 8/35; A61K 8/553; A61K 8/85
See application file for complete search history.

(56) References Cited

U.S. PATENT DOCUMENTS

| | | |
|---|---|---|
| 3,691,090 A | 9/1972 | Kitajima et al. |
| 4,460,563 A | 7/1984 | Calanchi |
| 4,599,379 A | 7/1986 | Flesher et al. |
| 4,628,078 A | 12/1986 | Glover et al. |
| 4,752,496 A | 6/1988 | Fellows et al. |
| 4,835,206 A | 5/1989 | Farrar et al. |
| 4,849,484 A | 7/1989 | Heard |
| 5,051,304 A | 9/1991 | David et al. |
| 5,100,660 A | 3/1992 | Hawe et al. |
| 6,203,802 B1 | 3/2001 | Handjani et al. |
| 9,095,543 B2 | 8/2015 | Susak et al. |
| 2003/0084914 A1 | 5/2003 | Simon |
| 2007/0065379 A1 | 3/2007 | Biatry et al. |
| 2009/0047341 A1 | 2/2009 | Simmonet et al. |
| 2015/0313809 A1 | 11/2015 | Lynch et al. |
| 2018/0110254 A1 | 4/2018 | Gierke et al. |

FOREIGN PATENT DOCUMENTS

| | | |
|---|---|---|
| EP | 0228868 A2 | 7/1987 |
| FR | 2795928 A1 | 1/2001 |
| JP | 2007223936 A | 9/2007 |
| KR | 20190043307 A * | 4/2019 |

OTHER PUBLICATIONS

Machine translation of KR20190043307A, 2019, pp. 1-33 (Year: 2019).*

* cited by examiner

*Primary Examiner* — Andrew S Rosenthal
(74) *Attorney, Agent, or Firm* — Polsinelli PC

(57) ABSTRACT

The ceramide composition includes capsules dispersed in the ceramide composition, the capsules comprising a shell and a core. The shell includes a polycaprolactone, a block copolymer, and a surfactant. The core includes ceramide NP, hydroxypalmitoyl sphinganine, 2-oleamido-1,3-octadecanediol, and a hydrophobic solvent. The core has a weight ratio of the ceramide NP of (i) and the hydroxypalmitoyl sphinganine of (ii) to the 2-oleamido-1,3-octadecanediol of (iii) is from 1:2.5 to 1:5. Additionally, the ceramide composition includes hydroxyacetophenone and hydrophilic solvent.

20 Claims, No Drawings

CERAMIDE CONTAINING CAPSULES, CERAMIDE COMPOSITIONS, AND COSMETIC COMPOSITIONS THEREOF

FIELD OF THE DISCLOSURE

The instant disclosure relates to ceramide containing capsules, ceramide compositions including such ceramide containing capsules, and cosmetic compositions produced therefrom. Additionally, the instant disclosure relates to methods for producing the ceramide compositions and ceramide containing capsules.

BACKGROUND OF THE DISCLOSURE

Skin acts as a natural barrier between internal and external environments and therefore plays an important role in vital biological functions such as protection against mechanical and chemical injury, micro-organisms, and ultraviolet damage. Human skin is made up mainly of two main layers, the dermis and the epidermis, which superficially covers the dermis. The dermis provides the epidermis with a solid support. The dermis is composed mainly of fibroblasts and an extracellular matrix of collagen, elastin, and a substance known as ground substance. These components are synthesized by the fibroblasts.

The epidermis, which covers the dermis and is in direct contact with the external environment, has the main role of protecting the body against the dehydration and external attack. Natural human epidermis is composed mainly of three types of cells, namely keratinocytes, which form the vast majority, melanocytes and Langerhans cells. Each of these cell types contributes to protecting the body against external attacking factors (the weather, ultraviolet rays, tobacco, etc.). The epidermis is a keratinized, stratified pavement of epithelium that is about 90% keratinocytes. The gradual differentiation of the cells of the basal membrane, which separates the dermis from the epidermis, towards the surface of the epidermis includes the differentiation of keratinocytes, which migrate towards the surface of the skin, where they desquamate.

Ageing of the epidermis results in a reduction of thickness. Atrophy of the epidermis is the consequence of the slowing down of keratinocyte proliferation and of the accumulation of senescent keratinocytes. The outer layer becomes dull. The cells constituting the epidermis are delimited by a lipid domain. In the course of differentiation, phospholipids, the role of which consists in producing the fluid structure of the cell membranes of the living layers of the epidermis, are gradually replaced by a mixture composed predominantly of fatty acids, cholesterol and ceramides (sphingolipids).

These lipids are organized in specific lamellar structures, the integrity of which depends on the quality of the fractions present, but also on their respective proportions. This lamellar structure of the lipids of the lipid domain of the epidermis is responsible for the fluidity and thus the suppleness of the skin. The lipids are also responsible for the "barrier" properties of the epidermis, particularly of the stratum corneum.

The epidermal lipids are mainly synthesized in living epidermis. They are made up mainly of phospholipids, sphingolipids, cholesterol, free fatty is acids, triglycerides, cholesterol esters and alkanes. The phospholipids are essential for the constitution of cell membranes. They play an important role in the mediation of extracellular signals and the formation of free aliphatic chains used for energy production. They constitute a reservoir of free fatty acids necessary for the constitution of the sphingolipids. The cholesterol plays a fundamental role in moisturization of the skin and in the "barrier" function of the epidermis. Free fatty acids play a major role in maintaining the lamellar structure of the lipids of the stratum corneum, and also in the constitution of cell membranes, where they are responsible for the membrane fluidity, but also for physiological processes such as the functioning of receptors or enzymatic activity.

Ceramides are lipids that play a paramount role in the metabolism of the epidermis, and are necessary for maintaining the multilamellar structure of the intercorneocytic lipids. They are also essential for the "barrier" function of the epidermis and for water exchanges, especially for overcoming age-related moisturization problems.

Accordingly, improved compositions and products that deliver ceramides to skin are needed.

SUMMARY OF THE DISCLOSURE

The instant disclosure relates to ceramide containing capsules, ceramide compositions including such ceramide containing capsules, and cosmetic compositions produced from either of the foregoing. It is well-recognized that it is difficult to incorporate ceramides into cosmetic compositions, and particularly cosmetic compositions having large amounts of water. The ceramide containing capsules and ceramide compositions disclosed herein advantageously enable ceramides to be easily incorporated into various types of cosmetic compositions, including water based cosmetic compositions via the addition of the ceramide compositions and/or ceramide containing capsules.

The ceramide compositions preferably improve the appearance and/or functionality of skin. For example, cosmetic compositions having the ceramide compositions may provide improved skin barrier functionality to a user's skin. In some instances, the ceramide compositions promote regeneration, renewal, repair and/or improved moisture retention of compromised skin, e.g., when the ceramide compositions are incorporated into a cosmetic composition and applied to the compromised skin. In further instances, the ceramide compositions and cosmetic compositions produced therefrom provide improved skin appearance, such as anti-inflammation, improved skin pigmentation, etc.

The inventors discovered a unique mixture of ceramides in specific weight ratios that provide enhanced stability, and surprisingly may be used with hydroxyacetophenone as a preservative instead of, e.g., phenoxyethanol and/or penylethylalcohol. For example, the ceramide compositions and/or cosmetic compositions may be free of or essentially free of phenoxyethanol. In some instances, the ceramide and/or cosmetic composition includes 3 wt. % or less, 2 wt. % or less, or 1 wt. % or less of phenoxyethanol, based on the total weight of the respective composition. In another instance, the ceramide and/or cosmetic compositions include about 0 wt. % of phenoxyethanol, based on the respective weight of the composition. The ceramide and/or cosmetic composition may also be free of or essentially free of penylethylalcohol. The ceramide and/or cosmetic compositions may include 3 wt. % or less, 2 wt. % or less, or 1 wt. % or less of penylethylalcohol, based on the respective weight of the composition. In at least one case, the ceramide and/or cosmetic compositions include about 0 wt. % of penylethylalcohol, based on the respective weight of the composition. Additionally or alternatively, the ceramide and/or cosmetic compositions may be free or essentially free of all preservatives other than hydroxyacetophenone. In some instances, the ceramide and/or cosmetic composition includes 3 wt. % or less, 2 wt. % or less, 1 wt. % or less, or about 0 wt. % of preservatives other than hydroxyacetophenone, based on the respective weight of the composition.

In accordance with an aspect of the disclosure, provided is a ceramide composition comprising ceramide containing capsules. The ceramide composition of the instant disclosure typically include:
(I) capsules dispersed in the ceramide composition, the capsules comprising:
 (a) a shell comprising:
  (i) a polycaprolactone,
  (ii) a block copolymer, and
  (iii) a surfactant, and
 (b) a core comprising:
  (i) ceramide NP,
  (ii) hydroxypalmitoyl sphinganine,
  (iii) 2-oleamido-1,3-octadecanediol,
   wherein a weight ratio of the ceramide NP of (i) and the hydroxypalmitoyl sphinganine of (ii) to the 2-oleamido-1,3-octadecanediol of (iii) is from 1:2.5 to 1:5, and
  (iv) hydrophobic solvent;
(II) hydroxyacetophenone; and
(III) hydrophilic solvent.

The capsules of ceramide composition may be have an average diameter of about 200 to about 400 nm. The capsules may include a shell comprising a surfactant that includes a phospholipid group.

The core of the capsules typically include ceramide NP, hydroxypalmitoyl sphinganine, 2-oleamido-1,3-octadecanediol, and a hydrophobic solvent. In some instances the core of the capsules comprises (i) about 2 to about 8 wt. % of ceramide NP, (ii) about 2 to about 8 wt. % of hydroxypalmitoyl sphinganine, (iii) about 10 to about 40 wt. % of 2-oleamido-1,3-octadecanediol, and (iv) about 44 to about 86 wt. % of hydrophobic solvent, wherein the foregoing weight percentages of (i)-(iv) are based on the total weight of the core of (b). Additionally or alternatively, the weight ratio of the ceramide NP of (i) and the hydroxypalmitoyl sphinganine of (ii) to the 2-oleamido-1,3-octadecanediol of (iii) may range from 1:2.5 to 1:4, 1:2.6 to 1:4, 1:2.7 to 1:4, or 1:2.8 to 1:4. The core of the capsules may further comprise a ceramide or derivative thereof selected from at least one ceramide and/or a derivative thereof selected from ceramide-EOS, ceramide-NS, ceramide-EOH, ceramide-AS, ceramide-NH, ceramide-AP, ceramide-AH, Ceramide-OS, ceramide-OH, and a mixture thereof.

The hydrophobic solvent, preferably, comprises a fatty alcohol. For example, the fatty alcohol may be selected from cetearyl alcohol, cetyl alcohol, stearyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, octyldodecanol, 2-octyl-1-dodecanol, and a mixture thereof. In some instances the fatty alcohol is 2-octyl-1-dodecanol.

The ceramide composition may have a hydrophilic solvent comprising water. In some instances, the ceramide composition may be free of phenoxyethanol. The ceramide composition may additionally or alternatively be free of penylethylalcohol. In some cases, the ceramide composition may further comprise at least one of (IV) an emulsifier; (V) a polyol; (VI) a fatty compound; and (VII) a monoalcohol.

In accordance with another aspect of the disclosure, provided is a cosmetic composition containing the ceramide composition. The cosmetic composition typically includes:
(A) about 1% to about 20 wt. % of a ceramide composition, the ceramide composition comprising:
 (I) capsules dispersed in the ceramide composition, the capsules comprising:
  (a) a shell comprising:
   (i) a polycaprolactone,
   (ii) a block copolymer, and
   (iii) a surfactant, and
  (b) a core comprising:
   (i) ceramide NP,
   (ii) hydroxypalmitoyl sphinganine,
   (iii) 2-oleamido-1,3-octadecanediol,
    wherein a weight ratio of the ceramide NP of (i) and the hydroxypalmitoyl sphinganine of (ii) to the 2-oleamido-1,3-octadecanediol of (iii) is from 1:2.5 to 1:5, and
   (iv) hydrophobic solvent,
 (II) hydroxyacetophenone, and
 (III) hydrophilic solvent;
(B) optionally, an emulsifier;
(C) optionally, a polyol;
(D) optionally, a fatty compound; and
(E) optionally, a monoalcohol.

The cosmetic compositions, preferably, improve the skin barrier function.

In accordance with a further aspect of the disclosure, a method is provided for producing the ceramide composition. Typically, the methods for producing ceramide compositions include:
(I) providing a mixture at ambient temperature comprising:
 (a) an oily phase comprising:
  (i) ceramide NP,
  (ii) hydroxypalmitoyl sphinganine,
  (iii) 2-oleamido-1,3-octadecanediol, and
   wherein a weight ratio of the ceramide NP of (i) and the hydroxypalmitoyl sphinganine of (ii) to the 2-oleamido-1,3-octadecanediol of (iii) is from 1:2.5 to 1:5, and
  (iv) hydrophobic solvent,
 (b) a liposome precursor that is immiscible with water and with the oily phase, wherein the liposome precursor comprises:
  (i) a polycaprolactone, and
  (ii) a surfactant,
 (c) acetone, wherein a weight ratio of the oily phase of (a) and the liposome precursor of (b) to the acetone of (c) is 1:20 to about 1:40,
(II) homogenizing the oily phase and the liposome precursor at a temperature of 30° C. or more;
(III) dispersing, the homogeneous mixture of (II) in a preheated aqueous phase, in order to obtain an emulsion, the preheated aqueous phase comprising a block copolymer;
(IV) distilling the solvent of (III) to remove acetone and concentrate from the mixture for the coacervation of the liposome precursor and for the coating of drops of the said oily phase by the coacervates to obtain a suspension;
(V) cooling the suspension of step (IV) to a temperature for the formation of capsules by the precipitation and/or crystallization of the coacervates; and
(VI) adding hydroxyacetophenone.

In some instances, the polycaprolactone has a weight average molecular weight of about 400 to about 10,000. The polycaprolactone may comprise up to 100 monomer units. Additionally or alternatively, the weight ratio of the ceramide NP of (i) and the hydroxypalmitoyl sphinganine of (ii) to the 2-oleamido-1,3-octadecanediol of (iii) is from 1:2.5 to 1:4.

DETAILED DESCRIPTION OF THE DISCLOSURE

The instant disclosure relates to ceramide containing capsules, ceramide compositions including such ceramide containing capsules, and cosmetic compositions produced therefrom. Additionally, the instant disclosure relates to methods for producing the ceramide compositions and ceramide containing capsules.

Ceramide Compositions

The ceramide containing capsules and ceramide compositions advantageously enable ceramides to be easily incorporated into various types of cosmetic compositions, including aqueous based cosmetic compositions.

The ceramide compositions typically include:
(I) capsules dispersed in the ceramide composition, the capsules comprising:
  (a) a shell comprising:
    (i) a polycaprolactone,
    (ii) a block copolymer, and
    (iii) a surfactant, and
  (b) a core comprising:
    (i) ceramide NP,
    (ii) hydroxypalmitoyl sphinganine,
    (iii) 2-oleamido-1,3-octadecanediol,
      wherein a weight ratio of the ceramide NP of (i) and the hydroxypalmitoyl sphinganine of (ii) to the 2-oleamido-1,3-octadecanediol of (iii) is from 1:2.5 to 1:5 ([(i)+(ii)]:(iii)), and
    (iv) hydrophobic solvent;
(II) hydroxyacetophenone; and
(III) hydrophilic solvent.

(I) Capsules

The ceramide compositions include ceramide containing capsules dispersed in the ceramide composition. Although the ceramide compositions may be prepared to have capsules of various sizes, the capsules typically have an average diameter of about 100 μm or less. For example, the capsules may have an average diameter of about 90 μm or less, about 80 μm or less, about 70 μm or less, about 60 μm or less, about 50 μm or less, about 40 μm or less, about 30 μm or less, about 20 μm or less, about 10 μm or less, or about 1 μm or less. The capsules may be prepared to have an average diameter of less than 1 μm or less, e.g., to reduce the tactile feel of individual capsules to a user. In some instances, the capsules may have an average diameter of about 50 nm to about 900 nm, about 50 nm to about 800 nm, about 50 nm to about 700 nm, about 50 nm to about 600 nm, about 50 nm to about 500 nm, about 50 nm to about 400 nm, about 50 nm to about 300 nm, about 50 nm to about 200 nm; about 100 nm to about 900 nm, about 100 nm to about 800 nm, about 100 nm to about 700 nm, about 100 nm to about 600 nm, about 100 nm to about 500 nm, about 100 nm to about 400 nm, about 100 nm to about 300 nm, about 100 nm to about 200 nm; about 200 nm to about 900 nm, about 200 nm to about 800 nm, about 200 nm to about 700 nm, about 200 nm to about 600 nm, about 200 nm to about 500 nm, about 200 nm to about 400 nm, or about 200 nm to about 300 nm, including ranges and sub-ranges thereof. The capsules may be prepared to have sizes that falls within ranges derived from any of the end-points described herein.

Additional disclosure relating to the ceramide containing capsules, ceramide compositions and methods for producing capsules may be found in US Patent Publication no. 20030084914; US Patent Publication no. 20070065379; U.S. Pat. Nos. 3,691,090; 4,460,563; 4,752,496; 5,051,304; Japanese Patent Publication no. 5285210; Japanese Patent Publication no. 8325117; and French Patent Publication no. 2795928, which are each incorporated herein in their entirety for all purposes.

(a) Shell

The capsules comprise a shell and a core. The shell of the capsules typically encapsulate the core, e.g., such that the core is contained within the shell. In some instances, the shell of the capsules totally encapsulate the liquid core at its periphery. The shell generally comprises a polycaprolactone, a block copolymer, and a surfactant.

(i) polycaprolactone

The shell of the capsules include a polycaprolactone. The amount of polycaprolactone in the she may vary, but typically is present in amount of about 1 to about 70 wt. % based on the total weight of the shell. For example, the amount of polycaprolactone in the shell may be about 10 to about 70 wt. %, about 20 to about 70 wt. %, about 30 to about 70 wt. %, about 40 to about 70 wt. %, about 50 to about 70 wt. %; about 10 to about 60 wt. %, about 20 to about 60 wt. %, about 30 to about 60 wt. %, about 40 to about 60 wt. %; about 10 to about 50 wt. %, about 20 to about 50 wt. %, about 30 to about 50 wt. %, about 40 to about 50 wt. %; about 10 to about 40 wt. %, about 20 to about 40 wt. %, about 30 to about 40 wt. %, including all ranges and subranges therein, based on the total weight of the components of the shell.

The polycaprolactone may be chosen from a polycaprolactone having a weight average molecular weight of 100 to 900,000. In some instances, the polycaprolactone has a weight average molecular weight of 100 to 900,000; 200 to 900,000; 400 to 900,000; 700 to 900,000; 1,000 to 900,000; 10,000 to 900,000; 50,000 to 900,000; 75,000 to 900,000; 100,000 to 900,000; 200,000 to 900,000; 400,000 to 900,000; 600,000 to 900,000; 700,000 to 900,000; from 100 to 800,000; 200 to 800,000; 400 to 800,000; 700 to 800,000; 1,000 to 800,000; 10,000 to 800,000; 50,000 to 800,000; 75,000 to 800,000; 100,000 to 800,000; 200,000 to 800,000; 400,000 to 800,000; 600,000 to 900,000; from 100 to 700,000; 200 to 700,000; 400 to 700,000; 700 to 700,000; 1,000 to 700,000; 10,000 to 700,000; 50,000 to 700,000; 75,000 to 700,000; 100,000 to 700,000; 200,000 to 700,000; 400,000 to 700,000; from 100 to 600,000; 200 to 600,000; 400 to 600,000; 700 to 600,000; 1,000 to 600,000; 10,000 to 600,000; 50,000 to 600,000; 75,000 to 600,000; 100,000 to 600,000; 200,000 to 600,000; 400,000 to 600,000; from 100 to 500,000; 200 to 500,000; 400 to 500,000; 700 to 500,000; 1,000 to 500,000; 10,000 to 500,000; 50,000 to 500,000; 75,000 to 500,000; 100,000 to 500,000; or 200,000 to 500,000, including all ranges and subranges therein. In other instances, the polycaprolactone has a weight average molecular weight of 100 to 20,000; 200 to 20,000; 400 to 20,000; 700 to 20,000; 1,000 to 20,000; from 100 to 15,000; 200 to 15,000; 400 to 15,000; 700 to 15,000; 1,000 to 15,000; from 100 to 10,000; 200 to 10,000; 400 to 10,000; 700 to 10,000; 1,000 to 10,000; from 100 to 5,000; 200 to 5,000; 400 to 5,000; 700 to 5,000; 1,000 to 5,000, including all ranges and subranges therein. Additionally and/or alternatively, the polycaprolactone comprises up to 100 monomer units. For example, the polycaprolactone may comprise up to 80 monomer units, up to 70 monomer units, up to 60 monomer units, up to 50 monomer units, or up to 40 monomer units.

The shell of the capsules may include a polycaprolactone that is substituted or unsubstituted. In some instances, the polycaprolactone is selected from polycaprolactone diols. For instance, the polycaprolactone may be commercially available under the tradename, CAPA™, which is manufactured by Perstorp.

(ii) A Block Copolymer,

The amount of block copolymer in the shell may vary, but typically ranges from about 1 to about 70 wt. % based on the total weight of the shell. For example, the amount of block copolymer in the shell may be about 10 to about 70 wt. %, about 20 to about 70 wt. %, about 30 to about 70 wt. %, about 40 to about 70 wt. %, about 50 to about 70 wt. %; about 10 to about 60 wt. %, about 20 to about 60 wt. %, about 30 to about 60 wt. %, about 40 to about 60 wt. %; about 10 to about 50 wt. %, about 20 to about 50 wt. %, about 30 to about 50 wt. %, about 40 to about 50 wt. %; about 10 to about 40 wt. %, about 20 to about 40 wt. %, about 30 to about 40 wt. %, including all ranges and subranges therein, based on the total weight of the shell.

The block copolymer may be chosen from a block copolymer having a weight average molecular weight of 1,000 to 900,000. In some instances, the block copolymer has a weight average molecular weight from 1,000 to 900,000; 10,000 to 900,000; 50,000 to 900,000; 75,000 to 900,000; 100,000 to 900,000; 200,000 to 900,000; 400,000 to 900,000; 600,000 to 900,000; 700,000 to 900,000; from 1,000 to 800,000; 10,000 to 800,000; 50,000 to 800,000; 75,000 to 800,000; 100,000 to 800,000; 200,000 to 800,000; 400,000 to 800,000; 600,000 to 900,000; from 1,000 to 700,000; 10,000 to 700,000; 50,000 to 700,000; 75,000 to 700,000; 100,000 to 700,000; 200,000 to 700,000; 400,000 to 700,000; from 1,000 to 600,000; 10,000 to 600,000; 50,000 to 600,000; 75,000 to 600,000; 100,000 to 600,000; 200,000 to 600,000; 400,000 to 600,000; from 1,000 to 500,000; 10,000 to 500,000; 50,000 to 500,000; 75,000 to 500,000; 100,000 to 500,000; or 200,000 to 500,000, including all ranges and subranges therein.

Preferably, the block copolymer is a poloxamer. In some instances, the poloxamer has a structure in accordance with the following formula:

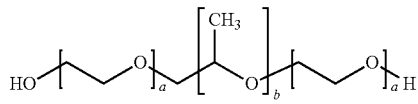

wherein a is an integer of from 10 to 110 and b is an integer of from 20 to 60. In some cases, a may be 12 and/or b may be 20. When a is 12 and b is 20, this is known as poloxamer 124. In other cases, a may be 80 and/or b may be 27. When a is 80 and b is 27, this is known as poloxamer 188. Additional poloxamers that may be useful include, e.g., poloxamer 108, poloxamer 182, poloxamer 183, poloxamer 212, poloxamer 217, poloxamer 238, poloxamer 288, poloxamer 331, poloxamer 338, poloxamer 335, and poloxamer 407.

(iii) a surfactant.

The shell comprises a surfactant in an amount that may vary, but is typically present in an amount of about 10 to about 70 wt. %, based on the total weight of the shell. For example, the amount of surfactant in the shell may be about 10 to about 70 wt. %, about 20 to about 70 wt. %, about 30 to about 70 wt. %, about 40 to about 70 wt. %, about 50 to about 70 wt. %; about 10 to about 60 wt. %, about 20 to about 60 wt. %, about 30 to about 60 wt. %, about 40 to about 60 wt. %; about 10 to about 50 wt. %, about 20 to about 50 wt. %, about 30 to about 50 wt. %, about 40 to about 50 wt. %; about 10 to about 40 wt. %, about 20 to about 40 wt. %, about 30 to about 40 wt. %, including all ranges and subranges therein, based on the total weight of the components of the shell.

The surfactant is preferably chosen from phospholipid surfactants. For example, the surfactant may comprise or be selected from lecithin. In some instances, the surfactant may include a proportion of lecithin or lecithin fractions, lysolecithin (such as hydrolyzed lecithin, enzymatically treated lecithin). The lecithin may be obtained from natural sources of any vegetable or animal source, such as, e.g., eggs, soy, sunflowers, rapeseed, etc. Non-limiting examples of commercial lecithin products include, e.g., soy lecithins, such as Lecico F 600, Lecico F 580, Lecico F300, Lecico F 200, Lecico F 100, Lecico P900, Lecico P 700, Lecico P 300; the sunflower lecithins, such as Lecico SUN 400, Lecico SUN FM 580; rapeseed lecithin, such as Lecico RAP 200. Additional disclosure relating to lecithin, surfactants, and capsules may be found in US Patent Publication no. 20180110254, which is incorporated herein in its entirety for all purposes. Additionally or alternatively, the surfactant may be chosen from coating surfactants, such as those taught by US Patent Publication no. 2015/0313809, which is incorporated herein, in its entirety, for all purposes.

(iv) Water-Soluble Polymers

The shell, optionally, may include a water-soluble polymer. The water-soluble polymer may chosen from poly(vinyl alcohol), polyvinyl-pyrrolidone, carboxymethylcellulose, poly(carboxylic acid)s and the crosslinked derivatives thereof. Additionally or alternatively, the water-soluble polymer may be chosen from natural gums, such as xanthans, starch, sodium alginate, pectins, chitosan, guar, locust bean, carrageenan or hyaluronic acid.

The water-soluble polymer may be included in the shell, if present, in an amount ranging from 0.001 to 10 wt. %, based on the total weight of the components comprising the shell. For example, the water-soluble polymer may be in an amount ranging from 0.001 to 10 wt. %, 0.01 to 10 wt. %, 0.1 to 10 wt. %, 1 to 10 wt. %, 2 to 10 wt. %, 3 to 10 wt. %, 4 to 10 wt. %, 5 to 10 wt. %; 0.01 to 8 wt. %, 0.01 to 8 wt. %, 0.1 to 8 wt. %, 1 to 8 wt. %, 2 to 8 wt. %, 3 to 8 wt. %, 4 to 8 wt. %, 5 to 8 wt. %; 0.001 to 6 wt. %, 0.01 to 6 wt. %, 0.1 to 6 wt. %, 1 to 6 wt. %, 2 to 6 wt. %, 3 to 6 wt. %; 0.001 to 4 wt. %, 0.01 to 4 wt. %, 0.1 to 4 wt. %, 1 to 4 wt. %, 2 to 4 wt. %, including all ranges and subranges therein, based on the total weight of the components of the shell.

(a) Core

The core of the capsules include a mixture of ceramides, typically including (i) ceramide NP, (ii) hydroxypalmitoyl sphinganine, (iii) 2-oleamido-1,3-octadecanediol, and (iv) hydrophobic solvent (octyldodecanol). Further description of the mixture of ceramides and the hydrophobic solvent is provided below.

(i)-(iii) Mixture of Ceramides

The core of the capsules includes ceramide NP, hydroxypalmitoyl sphinganine, and 2-oleamido-1,3-octadecanediol, in a weight ratio of the ceramide NP of (i) and the hydroxypalmitoyl sphinganine of (ii) to the 2-oleamido-1,3-octadecanediol of (iii) being from 1:2.5 to 1:5. Preferably, the weight ratio of the ceramide NP of (i) and the hydroxypalmitoyl sphinganine of (ii) to the 2-oleamido-1,3-octadecanediol of (iii) is from 1:2.5 to 1:4, 1:2.6 to 1:4, 1:2.7 to 1:4, 1:2.8 to 1:4, 1:2.9 to 1:4, 1:3 to 1:4, 1:3.1 to 1:4, 1:3.2 to 1:4, 1:3.3 to 1:4, 1:3.4 to 1:4. In some instances, the weight ratio of the ceramide NP of (i) and the hydroxypalmitoyl sphinganine of (ii) to the 2-oleamido-1,3-octadecanediol of (iii) is from 1:2.5 to 1:4, 1:2.5 to 1:3.9, 1:2.5 to 1:3.8, 1:2.5 to 1:3.7, 1:2.5 to 1:3.6, 1:2.5 to 1:3.5, 1:2.5 to 1:3.4, 1:2.5 to 1:3.3, or 1:2.5 to 1:3.2.

The amount of ceramide NP in the core may vary, but typically is present in an amount of about 1 to about 15 wt. %, about 2 to about 15 wt. %, about 3 to about 15 wt. %, about 4 to about 15 wt. %, about 5 to about 15 wt. %, about 6 to about 15 wt. %, about 7 to about 15 wt. %; about 1 to about 13 wt. %, about 2 to about 13 wt. %, about 3 to about 13 wt. %, about 4 to about 13 wt. %, about 5 to about 13 wt. %, about 6 to about 13 wt. %, about 7 to about 13 wt. %; about 1 to about 11 wt. %, about 2 to about 11 wt. %, about 3 to about 11 wt. %, about 4 to about 11 wt. %, about 5 to about 11 wt. %, about 6 to about 11 wt. %, about 7 to about 11 wt. %; about 1 to about 9 wt. %, about 2 to about 9 wt. %, about 3 to about 9 wt. %, about 4 to about 9 wt. %, about 5 to about 9 wt. %, about 6 to about 9 wt. %, about 7 to about 9 wt. %; about 1 to about 8 wt. %, about 2 to about 8 wt. %, about 3 to about 8 wt. %, about 4 to about 8 wt. %, about 5 to about 8 wt. %, about 6 to about 8 wt. %; about 1 to about 6 wt. %, about 2 to about 6 wt. %, about 3 to about 6 wt. %, about 4 to about 6 wt. %, including all ranges and subranges therein, based on the total weight of the components of the core.

The amount of hydroxypalmitoyl sphinganine in the core may vary, but typically is present in an amount of about 1 to about 15 wt. %, about 2 to about 15 wt. %, about 3 to about 15 wt. %, about 4 to about 15 wt. %, about 5 to about 15 wt. %, about 6 to about 15 wt. %, about 7 to about 15 wt. %; about 1 to about 13 wt. %, about 2 to about 13 wt. %, about 3 to about 13 wt. %, about 4 to about 13 wt. %, about 5 to about 13 wt. %, about 6 to about 13 wt. %, about 7 to about 13 wt. %; about 1 to about 11 wt. %, about 2 to about 11 wt. %, about 3 to about 11 wt. %, about 4 to about 11 wt. %, about 5 to about 11 wt. %, about 6 to about 11 wt. %, about 7 to about 11 wt. %; about 1 to about 9 wt. %, about 2 to about 9 wt. %, about 3 to about 9 wt. %, about 4 to about 9 wt. %, about 5 to about 9 wt. %, about 6 to about 9 wt. %, about 7 to about 9 wt. %; about 1 to about 8 wt. %, about 2 to about 8 wt. %, about 3 to about 8 wt. %, about 4 to about 8 wt. %, about 5 to about 8 wt. %, about 6 to about 8 wt. %; about 1 to about 6 wt. %, about 2 to about 6 wt. %, about 3 to about 6 wt. %, about 4 to about 6 wt. %, including all ranges and subranges therein, based on the total weight of the components of the core.

The amount of 2-oleamido-1,3-octadecanediol in the core may vary, but typically is present in an amount of about 1 to about 60 wt. %, about 5 to about 60 wt. %, about 10 to about 60 wt. %, about 15 to about 60 wt. %, about 20 to about 60 wt. %, about 25 to about 60 wt. %, about 30 to about 60 wt. %; about 1 to about 50 wt. %, about 5 to about 50 wt. %, about 10 to about 50 wt. %, about 15 to about 50 wt. %, about 20 to about 50 wt. %, about 25 to about 50 wt. %, about 30 to about 50 wt. %; about 1 to about 40 wt. %, about 5 to about 40 wt. %, about 10 to about 40 wt. %, about 15 to about 40 wt. %, about 20 to about 40 wt. %, about 25 to about 40 wt. %, about 30 to about 40 wt. %; about 1 to about 35 wt. %, about 5 to about 35 wt. %, about 10 to about 35 wt. %, about 15 to about 35 wt. %, about 20 to about 35 wt. %, about 25 to about 35 wt. %; about 1 to about 30 wt. %, about 5 to about 30 wt. %, about 10 to about 30 wt. %, about 15 to about 30 wt. %, about 20 to about 30 wt. %, including all ranges and subranges therein, based on the total weight of the components of the core.

In some instances the mixture of ceramides in the core comprise: (i) about 2 to about 8 wt. % of ceramide NP, (ii) about 2 to about 8 wt. % of hydroxypalmitoyl sphinganine, and (iii) about 10 to about 40 wt. % of 2-oleamido-1,3-octadecanediol.

In addition to the ceramides discussed above, the core of capsules may be selected from or comprise one or more of ceramide 1, ceramide 2, ceramide 3, ceramide 4, ceramide 5, ceramide 1A, ceramide 6 II, ceramide AP, ceramide AH, ceramide EOP, ceramide EOS, ceramide NP, ceramide NH, ceramide NG, ceramide NS, ceramide OH, ceramide OS, ceramide AS, and/or ceramide NS dilaurate.

(iv) Hydrophobic Solvent

The core of the capsules include a hydrophobic solvent. The amount of hydrophobic solvent in the core may vary, but typically is present in amount of about 35 to about 90 wt. %, based on the total weight of the components of the core. For example, the amount of hydrophobic solvent present in the core may range from about 35 to about 90 wt. %, about 40 to about 90 wt. %, about 44 to about 90 wt. %, about 50 to about 90 wt. %, about 55 to about 90 wt. %, about 60 to about 90 wt. %, about 65 to about 90 wt. %, about 70 to about 90 wt. %, about 75 to about 90 wt. %; about 35 to about 86 wt. %, about 40 to about 86 wt. %, about 44 to about 86 wt. %, about 50 to about 86 wt. %, about 55 to about 86 wt. %, about 60 to about 86 wt. %, about 65 to about 86 wt. %, about 70 to about 86 wt. %, about 75 to about 86 wt. %; about 35 to about 80 wt. %, about 40 to about 80 wt. %, about 44 to about 80 wt. %, about 50 to about 80 wt. %, about 55 to about 80 wt. %, about 60 to about 80 wt. %, about 65 to about 80 wt. %, about 70 to about 80 wt. %; about 35 to about 75 wt. %, about 40 to about 75 wt. %, about 44 to about 75 wt. %, about 50 to about 75 wt. %, about 55 to about 75 wt. %, about 60 to about 75 wt. %, about 65 to about 75 wt. %; about 35 to about 70 wt. %, about 40 to about 70 wt. %, about 44 to about 70 wt. %, about 50 to about 70 wt. %, about 55 to about 70 wt. %, about 60 to about 70 wt. %, including all ranges and subranges therein, based on the total weight of the components of the core.

The hydrophobic solvent may be a fatty compound, such as oils, mineral oil, fatty alcohols, fatty acids, fatty alcohol derivatives, fatty acid derivatives, fatty esters, fatty ethers, waxes, etc. Preferably, the hydrophobic solvent is chosen from or comprises a fatty alcohol. For example, the fatty alcohol may be selected from cetearyl alcohol, cetyl alcohol, stearyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, octyldodecanol, 2-octyl-1-dodecanol, and a mixture thereof. In some instances the fatty alcohol is 2-octyl-1-dodecanol.

Non-limiting examples of fatty compounds are provided below:

Fatty Alcohols

The one or more fatty compounds may be glycerolated and/or oxyalkylenated, include from 8 to 30 carbon atoms, and/or be saturated or unsaturated. The fatty alcohols useful herein include those having from about 8 to about 30 carbon atoms, from about 12 to about 22 carbon atoms, and from about 14 to about 22 carbon atoms. These fatty alcohols can be straight or branched chain alcohols and can be saturated or unsaturated. Non-limiting examples of fatty alcohols include decyl alcohol, undecyl alcohol, dodecyl alcohol, myristyl alcohol, cetyl alcohol, stearyl alcohol, isostearyl alcohol, isocetyl alcohol, behenyl alcohol, linalool, oleyl alcohol, cis4-t-butylcyclohexanol, myricyl alcohol and a mixture thereof. In some cases, the fatty alcohols comprise at least one of or may be chosen from myristyl alcohol, cetyl alcohol, stearyl alcohol, isostearyl alcohol, oleyl alcohol, isotridecyl alcohol, and a mixture thereof.

The saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

The unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

Non-limiting examples of solid fatty alcohols include linear or branched, saturated or unsaturated alcohols containing from 8 to 30 carbon atoms, for example, myristyl alcohol, cetyl alcohol, stearyl alcohol and their mixture, cetylstearyl alcohol.

Fatty Esters

The fatty compounds of the ceramide composition may be liquid or solid fatty esters at 25° C., 1 atm. The fatty esters may include esters from a $C_6$-$C_3$2 fatty acid and/or a $C_6$-$C_{32}$ fatty alcohol. For example, the fatty compounds may include or be chosen from fatty acid monoesters and diesters, polyol esters, polyglycerol esters, polyglycerol polyricinoleate, polyglycerol poly-12-hydroxystearate, polyglycerol dimerate isostearate, ethylhexanoate, polyglycerol esters, and a mixture thereof. These esters may be esters of saturated or unsaturated, linear or branched $C_1$-$C_{26}$ aliphatic mono or polyacids and of saturated or unsaturated, linear or branched $C_1$-$C_{25}$ aliphatic mono or polyalcohols, the total number of carbon atoms in the esters being greater than or equal to 10. In one instance, the fatty compounds comprise one or more fatty acid monoesters. For the esters of mono-alcohols, at least one of the alcohol or the acid from which the esters result is branched. Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

In some instances, the fatty esters are cetyl esters, such as esters of saturated fatty acids and fatty alcohols. For example, the fatty esters may include or be chosen from cetyl palmitate, cetyl stearate, myristyl myristate, myristyl stearate, cetyl myristate, stearyl stearate, ceteary1 ethylhexanoate, and mixtures thereof. In one instance, the fatty esters may be one or more of or chosen from isopropyl isostearate, n-propyl myristate, isopropyl myristate, hexyl laurate, hexadecyl isostearate, hexydecyl laurate, hexyldecyl octanoate, n-propyl palmitate, isopropyl palmitate, and mixtures thereof. In another instance, the fatty esters include or may be chosen from diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, di pentaerythritol fatty acid ester, isopropyl myristate, octyldodecyl myristate, 2-hexyldecyl myristate, myristyl myristate, hexyldecyl di methyloctanoate, ethyl laurate, hexyl laurate, diisostearyl malate, dicaprylyl carbonate, cetearyl ethylhexanoate, and mixtures thereof. In yet a further instance, the ceramide composition includes one or more of or may have fatty compounds chosen from cetearyl alcohol, cetearyl ethylhexanoate, isopropyl myristate, and mixtures thereof.

Non-limiting examples of solid fatty acid esters and/or fatty acid esters that may be mentioned include solid esters obtained from $C_9$-$C_{26}$ fatty acids and from $C_9$-$C_{25}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

Non-limiting examples of liquid fatty acid include triglyceride oils of plant or synthetic origin, such as liquid fatty acid triglycerides containing 6 to 30 carbon atoms, for instance heptanoic or octanoic acid triglycerides, or alternatively, e.g., sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, coconut oil, camellina oil, tamanu oil, babassu oil and pracaxi oil, jojoba oil, shea butter oil, and mixtures thereof.

In one instance, the one or more fatty compounds include at least one of or are selected from fatty acid triglycerides, oils, mineral oil, alkanes, fatty alcohols, fatty acids, fatty alcohol derivatives, alkoxylated fatty acids, polyethylene glycol esters of fatty acids, propylene glycol esters of fatty acids, butylene glycol esters of fatty acids, esters of neopentyl glycol and fatty acids, polyglycerol/glycerol esters of fatty acids, glycol diesters, diesters of ethylene glycol and fatty acids, esters of fatty acids and fatty alcohols, esters of short chain alcohols and fatty acids, esters of fatty alcohols, hydroxy-substituted fatty acids, waxes, and a mixture thereof. In another instance, the one or more fatty compounds include one or more fatty acid triglycerides, such as caprylic/capric triglyceride.

Fatty Alcohol Derivatives

The ceramide compositions may, in some instances, include fatty alcohol derivatives such as alkyl ethers of fatty alcohols, alkoxylated fatty alcohols, alkyl ethers of alkoxylated fatty alcohols, esters of fatty alcohols and a mixture thereof. Non-limiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcochol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described;

polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof. Liquid fatty ethers may be chosen from liquid dialkyl ethers such as dicaprylyl ether. The non-liquid fatty ethers may also be chosen from dialkyl ethers and in particular dicetyl ether and distearyl ether, alone or as a mixture.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used. Mention may be made in particular of diethyl sebacate; diisopropyl sebacate; diisopropyl adipate; di-n-propyl adipate; triisopropyl citrate; glyceryl trilactate; glyceryl trioctanoate; neopentyl glycol diheptanoate; and diethylene glycol diisononanoate.

Fatty Acid Derivatives

The ceramide compositions may, in some instances, include fatty acid derivatives. The fatty acid derivatives are defined herein to include fatty acid esters of the fatty alcohols as defined above, fatty acid esters of the fatty alcohol derivatives as discussed above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. In some cases, the fatty acid derivative may comprise or be chosen from alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), glyceryl esters (glycerol esters), alkyl ethers of fatty alcohols, fatty acid esters of alkyl ethers of fatty alcohols, fatty acid esters of alkoxylated fatty alcohols, fatty acid esters of alkyl ethers of alkoxylated fatty alcohols, esters of fatty alcohols, hydroxy-substituted fatty acids, waxes, triglyceride compounds, lanolin, and a mixture thereof.

Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof.

(II) Hydrophilic Solvent

The ceramide composition typically includes a hydrophilic solvent. The hydrophilic solvent is preferably selected such that the capsules may stably reside in the hydrophilic solvent. The hydrophilic solvent may comprise or be chosen from water, polyols, glycols, and/or any other suitable hydrophilic solvent disclosed herein. The hydrophilic solvent may be selected based on the intended cosmetic composition or product to be produced using the ceramide composition.

Non-limiting examples of polyols include those chosen from polyols having from 2 to 15 carbon atoms and at least two hydroxyl groups. Exemplary polyols that may be used in the ceramide composition include and/or may be chosen from alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; sorbitol; sorbitan; triacetin; and a mixture thereof.

The one or more polyols may be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In one instance, the one or more polyols include or are chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof. In another instance, the cosmetic composition includes or is chosen from caprylyl glycol, glycerin, and a mixture thereof.

The total amount of polyols in the ceramide composition may vary from, e.g., about 0.1 to about 99 wt. %, based on the total weight of the ceramide composition. For example, the total amount of polyols may be from about 0.1 to about 25 wt. %, about 0.1 to about 20 wt. %, from about 0.1 to about 15 wt. %, about 0.1 to about 10 wt. %, about 0.1 to about 8 wt. %, about 0.1 to about 6 wt. %, from about 2 to about 99 wt. % about 2 to about 25 wt. %, about 2 to about 20 wt. %, about 2 to about 15 wt. %, about 2 to about 10 wt. %, about 2 to about 8 wt. %, or about 2 to about 6 wt. %, from about 3 to about 99 wt. % about 3 to about 25 wt. %, about 3 to about 20 wt. %, about 3 to about 15 wt. %, about 3 to about 10 wt. %, about 3 to about 8 wt. %, or about 3 to about 6 wt. %, including ranges and sub-ranges therebetween, based on the total weight of the ceramide composition.

(III) Hydroxyacetophenone

The ceramide composition typically includes hydroxyacetophenone. The amount of hydroxyacetophenone in the ceramide composition may vary, but typically ranges from about 0.01 to about 10 wt. % based on the total weight of the ceramide composition. For example, the amount of hydroxyacetophenone present in the ceramide composition may range from about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %; 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %; 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %, including all ranges and subranges thereof, based on the total weight of the ceramide composition. The ceramide composition may include one or more preservatives in addition to the hydroxyacetophenone.

Cosmetic Composition

The instant disclosure also relates to cosmetic compositions that include the ceramide composition and/or the ceramide containing capsules disclosed herein. The cosmetic composition may be in the form of an oil-in-water emulsion, water-in-oil emulsion, a suspension, a solution, or the like.

The cosmetic compositions typically include:
(A) about 1% to about 20 wt. % of a ceramide composition, the ceramide composition comprising:
  (I) capsules dispersed in the ceramide composition, the capsules comprising:
    (a) a shell comprising:
      (i) a polycaprolactone,
      (ii) a block copolymer, and
      (iii) a surfactant, and
    (b) a core comprising:
      (i) ceramide NP,
      (ii) hydroxypalmitoyl sphinganine,
      (iii) 2-oleamido-1,3-octadecanediol,
        wherein a weight ratio of the ceramide NP of (i) and the hydroxypalmitoyl sphinganine of (ii) to the 2-oleamido-1,3-octadecanediol of (iii) is from 1:2.5 to 1:5, and
      (iv) hydrophobic solvent,
  (II) hydrophilic solvent, and
  (III) hydroxyacetophenone;
(B) optionally, an emulsifier;
(C) optionally, a polyol;
(D) optionally, a fatty compound; and
(E) optionally, a monoalcohol.

The cosmetic compositions preferably include an amount of the ceramide composition to improve the appearance and/or functionality of skin. In some instances, the cosmetic compositions provide improved skin barrier functionality to a user's skin. For example, the cosmetic composition may promote regeneration, renewal, and/or repair of compromised skin. Additionally or alternatively, the cosmetic compositions may provide improved skin appearance, such as anti-inflammation, improved skin pigmentation, etc.

Suitable components, such as those listed below, may be included or excluded from the formulations for the cosmetic compositions depending on the specific combination of other components, the form of the cosmetic compositions, and/or the use of the formulation (e.g., a lotion, a serum, gel, cream, etc.).

(A) Ceramide Composition

The amount of the ceramide composition in the cosmetic composition may vary, but typically is present in amount ranging from about 1% to about 20 wt. %, based on the total weight of the cosmetic composition. For example, the amount of ceramide composition in the cosmetic composition may range from about 1 to about 25 wt. %, about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %; about 3 to about 25 wt. %, about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 9 wt. %, about 3 to about 8 wt. %, about 3 to about 7 wt. %; about 5 to about 25 wt. %, about 5 to about 20 wt. %, about 5 to about 18 wt. %, about 5 to about 16 wt. %, about 5 to about 14 wt. %, about 5 to about 12 wt. %, about 5 to about 10 wt. %, about 5 to about 9 wt. %, about 5 to about 8 wt. %; about 8 to about 25 wt. %, about 8 to about 20 wt. %, about 8 to about 18 wt. %, about 8 to about 16 wt. %, about 8 to about 14 wt. %, about 8 to about 12 wt. %; about 10 to about 25 wt. %, about 10 to about 20 wt. %, about 10 to about 18 wt. %, about 10 to about 16 wt. %, about 10 to about 14 wt. %; about 13 to about 25 wt. %, about 13 to about 20 wt. %, about 13 to about 18 wt. %; about 15 to about 25 wt. %, about 15 to about 20 wt. %, about 15 to about 18 wt. %; about 18 to about 25 wt. %; about 20 to about 25 wt. %, based on the total weight of the cosmetic composition.

(B) Emulsifiers

The cosmetic compositions described herein include one or more emulsifiers. For example, the emulsifier may be an amphoteric, anionic, cationic or nonionic emulsifier, used alone or as a mixture, and optionally with a co-emulsifier. The emulsifiers are chosen in an appropriate manner according to the emulsion to be obtained.

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM 90™ by the company Goldschmidt.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

The one or more emulsifiers may be oxyalkylenated organosiloxane emulsifiers. The oxyalkylenated organosiloxane emulsifiers may be fully or partially crosslinked and/or be elastomeric or non-elastomeric. They are sometimes referred to as "emulsifying elastomers" because of they have both elastomeric and emulsifying properties. In some instances, the one or more emulsifiers include an oganosiloxane emulsifier, including crosslinked organosiloxane emulsifiers. For example, the cosmetic compositions may comprise one or more crosslinked organosiloxane emulsifier including or chosen from dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer, and mixtures thereof.

In another instance, the cosmetic compositions include one or more linear organosiloxane emulsifier chosen from cyclotetrasiloxane (and) cyclopentasiloxane (and) PEG/PPG-18 dimethicone, cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone; and mixtures thereof.

The cosmetic composition may, in some instances, include an oxyalkylenated organosiloxane emulsifier. The oxyalkylenated organosiloxane emulsifier may have a structure in accordance with the following general formula:

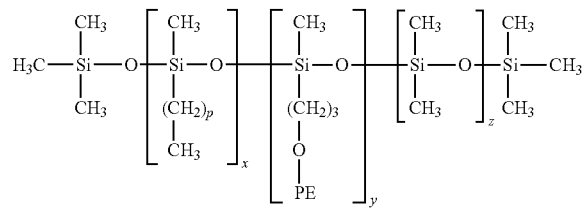

wherein p is 0-40 (the range including all numbers between and subranges such as 2, 3, 4, 13, 14, 15, 16, 17, 18, etc.), and PE is (—C2H4O)a-(—C3H6O)b-H wherein a is 0-25, b is 0-25 with the proviso that both a and b cannot be 0 simultaneously, x, y, and z are each independently ranging from 0 to 1 million with the proviso that x and y cannot be 0 simultaneously. In some instances, x, y, z, a, and b are such that the molecular weight of the polymer ranges from about 5,000 to about 500,000, from about 10,000 to 100,000, or is about 50,000, and the polymer is generically referred to as dimethicone copolyol. In additional instances, p is such that the long chain alkyl is cetyl or lauryl, and the compound is called, generically, cetyl dimethicone copolyol or lauryl dimethicone copolyol respectively. In some cases, the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or ether, such as methyl ether, ethyl ether, propyl ether, butyl ether, and the like.

The oxyalkylenated organosiloxane emulsifier may alternatively have a structure in accordance with the following general formula:

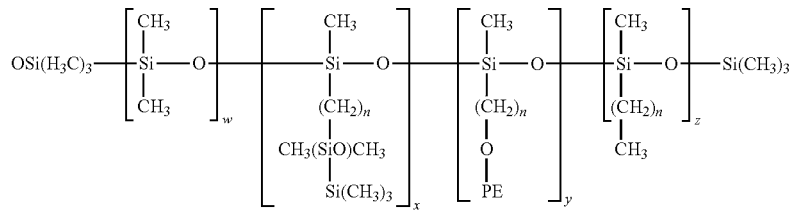

wherein each n is independently 0-100 with the proviso that there must be at least one PE radical. In some instances, where each n independently ranges from about 2 to 30, and PE (—C2H4O)a-(—C3H6O)b-H wherein a is 0-25, b is 0-25 with the proviso that both a and b cannot simultaneously be 0; and wherein w, x, y, and z are each independently 0 to 1,000,000 with the proviso that there is at least one PE. In some embodiments, the organosiloxane emulsifier is lauryl PEG-9 Polydimethylsiloxyethyl Dimethicone. Oxyalkylenated organosiloxane emulsifiers disclosed in U.S. Pat. No. 9,095,543 may be useful in the cosmetic compositions. U.S. Pat. No. 9,095,543 is incorporated herein by reference in its entirety for all purposes.

Further examples of organosiloxane emulsifiers include those having C.T.F.A. names Bis-Butyldimethicone Polyglyceryl-3; Bis-PEG/PPG-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; and mixtures thereof.

Further examples of commercial linear organosiloxane emulsifiers are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Further examples of cross-linked organosiloxane emulsifiers include, but are not limited to Dimethicone/dimethicone PEG/PPG 15 crosspolymer; Dimethicone PEG-10 crosspolymer; Dimethicone PEG-10/15 Crosspolymer; Dimethicone PEG-15 Crosspolymer; Dimethicone Polyglycerin-3 Crosspolymer; Dimethicone PPG-20 Crosspolymer; Dimethiconol/Methylsilanol/Silicate Crosspolymer; Dimethiconol/Silicate Crosspolymer; Lauryl Dimethicone PEG-15 Crosspolymer; Lauryl Dimethicone Polyglycerin-3 Crosspolymer; PEG-8 Dimethicone Polysorbate-20 Crosspolymer; PEG-10 Dimethicone/Vinyl Dimethicone Crosspolymer; PEG-10 Lauryl Dimethicone Crosspolymer; PEG-15/Lauryl Dimethicone Crosspolymer; and PEG-15 Laurylpolydimethylsiloxyethyl Crosspolymer.

The one or more emulsifiers may, in some instances, be polyoxyalkylenated silicone elastomers, such as, e.g., those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer. The polyglycerolated silicone elastomers may include or be chosen from dimethicone/polyglycerin-3 crosspolymer dispersed in dimethicone; or lauryl dimethicone/polyglycerin-3 crosspolymer dispersed in a variety of solvents such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

The emulsifiers may, in some instances, be nonionic a surfactant, such as one chosen from: alkanolamides; alkyl polyglucosides; polyoxyalkylenated nonionic surfactants; polyglycerolated nonionic surfactants; ethoxylated fatty esters; alcohols, alpha-diols, alkylphenols and esters of fatty acids, being ethoxylated, propoxylated or glycerolated; copolymers of ethylene oxide and/or of propylene oxide; condensates of ethylene oxide and/or of propylene oxide with fatty alcohols; polyethoxylated fatty amides; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

Additional nonionic surfactants that may, in some instances, be suitable include, e.g., alcohols, alpha-diols, alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol (C6-C24) alkylpolyglycosides; N—($C_6$-$C_{24}$)alkylglucamine derivatives, amine oxides such as (C10-C14)alkylamine oxides or N—($C_{10}$-$C_{14}$)acylaminopropylmorpholine oxides; and mixtures thereof.

In some cases, the nonionic surfactant may be chosen from esters of polyols with fatty acids with a saturated or unsaturated chain containing for example from 8 to 24 carbon atoms, and alkoxylated derivatives thereof; polyethylene glycol esters of a $C_8$-$C_{24}$; sorbitol esters of a $C_8$-$C_{24}$; sugar (sucrose, glucose, alkylglycose) esters of a $C_8$-$C_{24}$, preferably $C_{12}$-$C_{22}$, fatty acid or acids and alkoxylated derivatives thereof; ethers of sugar and a $C_8$-$C_{24}$, preferably $C_{12}$-$C_{22}$, fatty alcohol or alcohols; and mixtures thereof. In one instance, the nonionic surfactant is an ethoxylated fatty ester chosen from adducts of ethylene oxide with esters of lauric acid, palmitic acid, stearic acid or behenic acid, and mixtures thereof. Examples of ethoxylated fatty esters that may be suitable include those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

The nonionic surfactant may be chosen from glyceryl esters of fatty acids, glyceryl stearate (glyceryl mono-, di- and/or tristearate) (CTFA name: glyceryl stearate); glyceryl ricinoleate; glyceryl esters of $C_8$-$C_{24}$ alkoxylated fatty acids, such as polyethoxylated glyceryl stearate (glyceryl mono-, di- and/or tristearate), and PEG-20 glyceryl stearate; and mixtures thereof.

In some instances, the cosmetic composition may include an emulsifier such as dimers surfactants named "gemini surfactants," which may have two surfactant moieties identical or different, and constituted by a hydrophilic head group and a lipophilic group linked to each other through the head groups, thanks to a spacer. For example, the one or more emulsifiers may include or be chosen from those sold by Sasol company under the name CERALUTIOM, for example, CERALUTION H: Behenyl Alcohol, Glyceryl Stearate, Glyceryl Stearate Citrate et Sodium Dicocoyl ethylenediamine PEG-15 Sulfate, CERALUTION F: Sodium Lauroyl Lactylate et Sodium Dicocoyl ethylenediamine PEG-15 Sulfate, CERALUTION C: Aqua, Capric/Caprylic triglyceride, Ceteareth-25, Sodium Dicocoyl ethylenediamine PEG-15 Sulfate, Sodium Lauroyl Lactylate, Behenyl Alcohol, Glyceryl Stearate, Glyceryl Stearate Citrate, Gum Arabic, Xanthan Gum, Phenoxyethanol, Methylparaben, Ethylparaben, Butylparaben, Isobutylparaben. In at least one embodiment, the emulsifier of the cosmetic composition consists of sodium lauroyl lactylate or consists essentially of sodium lauroyl lactylate. In further embodiments, the emulsifier(s) of the cosmetic composition includes sodium lauroyl lactylate with one or more additional emulsifiers, such as a nonionic emulsifier or an anionic emulsifier.

The total amount of emulsifiers in the cosmetic compositions may vary from, e.g., about 0.001 to about 25 wt. %, based on the total weight of the composition. For example, the total amount of emulsifiers may be from about 0.001 to about 25 wt. %, about 0.001 to about 20 wt. %, from about 0.001 to about 15 wt. %, about 0.001 to about 10 wt. %, about 0.001 to about 8 wt. %, about 0.001 to about 6 wt. %, from about 0.5 to about 25 wt. % about 0.5 to about 20 wt. %, about 0.5 to about 15 wt. %, about 0.5 to about 10 wt. %, about 0.5 to about 8 wt. %, about 0.5 to 6 wt. %, from about 1 to about 25 wt. %, about 1 to about 20 wt. %, about 1 to about 15 wt. %, about 1 to about 10 wt. %, about 1 to about 8 wt. %, or about 1 to about 6 wt. %, from about 2 to about 25 wt. %, about 2 to about 20 wt. %, about 2 to about 15 wt. %, about 2 to about 10 wt. %, about 2 to about 8 wt. %, or about 2 to about 6 wt. %, from about 3 to about 25 wt. %, about 3 to about 20 wt. %, about 3 to about 15 wt. %, about 3 to about 10 wt. %, about 3 to about 8 wt. %, or about 3 to about 6 wt. %, from about 4 to about 25 wt. %, about 4 to about 20 wt. %, about 4 to about 15 wt. %, about 4 to about 10 wt. %, about 4 to about 8 wt. %, or about 4 to about 6 wt. %, from about 5 to about 25 wt. %, about 0.05 to about 20 wt. %, about 0.05 to about 15 wt. %, about 0.05 to about 10 wt. %, about 0.05 to about 8 wt. %, or about 0.05 to about 6 wt. % including ranges and sub-ranges therebetween, based on the total weight of the cosmetic composition. In one instance, the total amount of emulsifiers in the cosmetic composition are typically in an amount from 0.5, 0.6, 0.7, 0.8, 0.9 or 1.0 wt. % to 5, 6, 7, 8, 9, or 10 wt. %, based on the total weight of the cosmetic composition.

(C) Polyols

The polyols of the cosmetic composition may comprise or be chosen from polyols having from 2 to 15 carbon atoms and at least two hydroxyl groups. Exemplary polyols that may be used in the cosmetic composition include and/or may be chosen from alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; sorbitol; sorbitan; triacetin; and a mixture thereof.

The polyol(s) may be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In one instance, the one or more polyols include or are chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof. In another instance, the cosmetic composition includes or is chosen from caprylyl glycol, glycerin, and a mixture thereof.

The total amount of polyols in the ceramide composition may vary from, e.g., about 0.1 to about 99 wt. %, based on the total weight of the cosmetic composition. For example, the total amount of polyols may be from about 0.1 to about 25 wt. %, about 0.1 to about 20 wt. %, from about 0.1 to about 15 wt. %, about 0.1 to about 10 wt. %, about 0.1 to about 8 wt. %, about 0.1 to about 6 wt. %, from about 2 to about 99 wt. % about 2 to about 25 wt. %, about 2 to about 20 wt. %, about 2 to about 15 wt. %, about 2 to about 10 wt. %, about 2 to about 8 wt. %, or about 2 to about 6 wt. %, from about 3 to about 99 wt. % about 3 to about 25 wt. %, about 3 to about 20 wt. %, about 3 to about 15 wt. %, about 3 to about 10 wt. %, about 3 to about 8 wt. %, or about 3 to about 6 wt. %, including ranges and sub-ranges therebetween, based on the total weight of the cosmetic composition.

(D) Fatty Compound(s)

The cosmetic composition may include one or more fatty compounds, which may be liquid or solid at room temperature and at atmospheric pressure (25° C., 1 atm). Fatty compounds are typically organic compounds that are not soluble in water at normal temperature (25° C.) and at atmospheric pressure (750 mmHg) (solubility below 10%). In some instances, the solubility in water may be below 5%, below 1%, or below 0.1%.

The total amount of fatty compounds in the cosmetic composition may vary from, e.g., about 0.1 to about 25 wt. %, based on the total weight of the cosmetic composition. For example, the total amount of fatty compounds may be from about 0.1 to about 25 wt. %, about 0.1 to about 20 wt. %, from about 0.1 to about 15 wt. %, about 0.1 to about 10 wt. %, about 0.1 to about 8 wt. %, about 0.1 to about 6 wt. %, from about 0.5 to about 25 wt. % about 0.5 to about 20 wt. %, about 0.5 to about 15 wt. %, about 0.5 to about 10 wt. %, about 0.5 to about 8 wt. %, about 0.5 to 6 wt. %, from about 1 to about 25 wt. %, about 1 to about 20 wt. %, about 1 to about 15 wt. %, about 1 to about 10 wt. %, about 1 to about 8 wt. %, or about 1 to about 6 wt. %, from about 1.5 to about 25 wt. %, about 1.5 to about 20 wt. %, about 1.5 to about 15 wt. %, about 1.5 to about 10 wt. %, about 1.5 to about 8 wt. %, or about 1.5 to about 6 wt. %, from about 2 to about 25 wt. %, about 2 to about 20 wt. %, about 2 to about 15 wt. %, about 2 to about 10 wt. %, about 2 to about 8 wt. %, or about 2 to about 6 wt. %, from about 2.5 to about 25 wt. %, about 2.5 to about 20 wt. %, about 2.5 to about 15 wt. %, about 2.5 to about 10 wt. %, about 2.5 to about 8 wt. %, or about 2.5 to about 6 wt. %, from about 3 to about 25 wt. %, about 3 to about 20 wt. %, about 3 to about 15 wt. %, about 3 to about 10 wt. %, about 3 to about 8 wt. %, or about 3 to about 6 wt. %, from about 3.5 to about 25 wt. %, about 3.5 to about 20 wt. %, about 3.5 to about 15 wt. %, about 3.5 to about 10 wt. %, about 3.5 to about 8 wt. %, or about 3.5 to about 6 wt. %, including ranges and sub-ranges therebetween, based on the total weight of the cosmetic composition.

Non-limiting examples of fatty compounds of the cosmetic composition include or may be chosen from oils, mineral oil, fatty alcohols, fatty acids, fatty alcohol derivatives, fatty acid derivatives (e.g., alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), glyceryl esters (glycerol esters), alkyl ethers of fatty alcohols, fatty acid esters of alkyl ethers of fatty alcohols, fatty acid esters of alkoxylated fatty alcohols, fatty acid esters of alkyl ethers of alkoxylated fatty alcohols, esters of fatty alcohols, hydroxy-substituted fatty acids, waxes, triglyceride compounds, lanolin, and a mixture thereof. In some instances, the one or more fatty compound may comprise or be chosen from fatty alcohols, fatty acids, esters of fatty acids, and/or esters of fatty alcohols (e.g., cetyl palmitate, cetyl stearate, myristyl myristate, myristyl stearate, cetyl myristate, and stearyl stearate (a mixture of which is referred to as "cetyl esters")). Additionally or alternatively, the one or more fatty compounds may include or be chosen from hydrocarbons, fatty alcohols, fatty alcohol derivatives, fatty acids, fatty acid derivatives, fatty esters, fatty ethers, oils, waxes, etc. In one instance, the one or more fatty compounds is a hydrocarbon that is linear, branched, and/or cyclical, such as cyclic $C_6$-$C_{16}$ alkanes, hexane, undecane, dodecane, tridecane, and isoparaffins, for instance isohexadecane, isododecane and isodecane. Additionally, the linear or branched hydrocarbons may be composed only of carbon and hydrogen atoms of mineral, plant, animal or synthetic origin with more than 16 carbon atoms, such as volatile or non-volatile liquid paraffins, petroleum jelly, liquid petroleum jelly, polydecenes, hydrogenated polyisobutene, and squalane.

Fatty Alcohols

The one or more fatty compounds may be glycerolated and/or oxyalkylenated, may include from 8 to 30 carbon atoms, and may be saturated or unsaturated. The fatty alcohols useful herein include those having from about 8 to about 30 carbon atoms, from about 12 to about 22 carbon atoms, and from about 14 to about 22 carbon atoms. These fatty alcohols can be straight or branched chain alcohols and can be saturated or unsaturated. Non-limiting examples of fatty alcohols include decyl alcohol, undecyl alcohol, dodecyl alcohol, myristyl alcohol, cetyl alcohol, stearyl alcohol, isostearyl alcohol, isocetyl alcohol, behenyl alcohol, linalool, oleyl alcohol, cis4-t-butylcyclohexanol, myricyl alcohol and a mixture thereof. In some cases, the fatty alcohols comprise at least one of or may be chosen from myristyl alcohol, cetyl alcohol, stearyl alcohol, isostearyl alcohol, oleyl alcohol, isotridecyl alcohol, and a mixture thereof.

The saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

The unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

Non-limiting examples of solid fatty alcohols include linear or branched, saturated or unsaturated alcohols containing from 8 to 30 carbon atoms, for example, myristyl alcohol, cetyl alcohol, stearyl alcohol and their mixture, cetylstearyl alcohol.

Fatty Esters

The fatty compounds of the cosmetic composition may be liquid or solid fatty esters at 25° C., 1 atm. The fatty esters may include esters from a $C_6$-$C_{32}$ fatty acid and/or a $C_6$-$C_{32}$ fatty alcohol. For example, the fatty compounds may include or be chosen from fatty acid monoesters and diesters, polyol esters, polyglycerol esters, polyglycerol polyricinoleate, polyglycerol poly-12-hydroxystearate, polyglycerol dimerate isostearate, ethylhexanoate, polyglycerol esters, and a mixture thereof. These esters may be esters of saturated or unsaturated, linear or branched $C_1$-$C_{26}$ aliphatic mono or polyacids and of saturated or unsaturated, linear or branched $C_1$-$C_{25}$ aliphatic mono or polyalcohols, the total number of carbon atoms in the esters being greater than or equal to 10. In one instance, the fatty compounds comprise one or more fatty acid monoesters. For the esters of monoalcohols, at least one of the alcohol or the acid from which the esters result is branched. Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

In some instances, the fatty esters are cetyl esters, such as esters of saturated fatty acids and fatty alcohols. For example, the fatty esters may include or be chosen from cetyl palmitate, cetyl stearate, myristyl myristate, myristyl stearate, cetyl myristate, stearyl stearate, cetearyl ethylhexanoate, and mixtures thereof. In one instance, the fatty esters may be one or more of or chosen from isopropyl isostearate, n-propyl myristate, isopropyl myristate, hexyl laurate, hexadecyl isostearate, hexydecyl laurate, hexyldecyl octanoate, n-propyl palmitate, isopropyl palmitate, and mixtures thereof. In another instance, the fatty esters include or may be chosen from diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, di pentaerythritol fatty acid ester, isopropyl myristate, octyldodecyl myristate, 2-hexyldecyl myristate, myristyl myristate, hexyldecyl di methyloctanoate, ethyl laurate, hexyl laurate, diisostearyl malate, dicaprylyl carbonate, cetearyl ethylhexanoate, and mixtures thereof. In yet a further instance, the cosmetic composition includes one or more of or may have fatty compounds chosen from cetearyl alcohol, cetearyl ethylhexanoate, isopropyl myristate, and mixtures thereof.

Non-limiting examples of liquid fatty acid include triglyceride oils of plant or synthetic origin, such as liquid fatty acid triglycerides containing 6 to 30 carbon atoms, for instance heptanoic or octanoic acid triglycerides, or alternatively, e.g., sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, coconut oil, camellina oil, tamanu oil, babassu oil and pracaxi oil, jojoba oil, shea butter oil, and mixtures thereof.

Non-limiting examples of solid fatty acid esters and/or fatty acid esters that may be mentioned include solid esters obtained from $C_9$-$C_{26}$ fatty acids and from $C_9$-$C_{25}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

Fatty Alcohol Derivatives

The cosmetic compositions may, in some instances, include fatty alcohol derivatives such as alkyl ethers of fatty alcohols, alkoxylated fatty alcohols, alkyl ethers of alkoxylated fatty alcohols, esters of fatty alcohols and a mixture thereof. Non-limiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcocohl, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof. Liquid fatty ethers may be chosen from liquid dialkyl ethers such as dicaprylyl ether. The non-liquid fatty ethers may also be chosen from dialkyl ethers and in particular dicetyl ether and distearyl ether, alone or as a mixture.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used. Mention may be made in particular of diethyl sebacate; diisopropyl sebacate; diisopropyl adipate; di-n-propyl adipate; triisopropyl citrate; glyceryl trilactate; glyceryl trioctanoate; neopentyl glycol diheptanoate; and diethylene glycol diisononanoate.

Fatty Acid Derivatives

The cosmetic compositions may, in some instances, include fatty acid derivatives. The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof.

(E) Monoalcohol(s)

The cosmetic compositions include one or more monoalcohols having from 2 to 6 carbon atoms. For example, the one or more monoalcohols may include or be chosen from ethanol, propanol, butanol, pentanol, hexanol, isopropyl alcohol, cycohexanol, isobutyl alcohol, 2-methyl-2-butanol (2-methylbutan-2-ol), and a mixture thereof. In one instance, the one or more monoalcohols comprises ethanol and optionally one or more additional monoalcohols having from 2 to 6 carbon atoms. In another instance, the one or more monoalcohols includes only ethanol or essentially only ethanol.

The total amount of monoalcohols may vary but is typically from about 0.05 to about 70 wt. %, based on the total weight of the composition. For example, the total amount of monoalcohols is from about 0.05 to about 30 wt. %, about 0.5 to about 25 wt. %, about 1 to about 20 wt. %, about 1.5 to about 15 wt. %, about 2 to about 10 wt. %, about 2.5 to about 5 wt. %, including ranges and sub-ranges therebetween, based on the total weight of the cosmetic composition. Additionally or alternatively, the cosmetic compositions may include an amount of ethanol ranging from about 0.05 to about 30 wt. %, about 0.5 to about 25 wt. %, about 1 to about 20 wt. %, about 1.5 to 15 wt. %, about 2 to 10 wt. %, about 2.5 to about 5 wt. %, including ranges and sub-ranges therebetween, based on the total weight of the composition. The amount of ethanol in the cosmetic composition may be about 0.05 to about 30 wt. %, about 0.5 to about 25 wt. %, about 1 to about 20 wt. %, about 1.5 to about 15 wt. %, about 2 to about 10 wt. %, about 2.5 to about 5 wt. %, including ranges and sub-ranges therebetween, based on the total weight of the cosmetic composition.

Thickener(s)

The cosmetic compositions described herein may, optionally, include a thickener. The thickener may be in an amount of about 0.1 wt. % to about 20 wt. %, about 0.1 to about 10 wt. %, about 0.1 wt. % to about 9 wt. %, about 0.2 wt. % to about 9 wt. %, about 0.3 wt. % to about 9 wt. %, about 0.4 wt. % to about 8 wt. %, about 0.5 wt. % to about 5 wt. %, about 1 wt. % to about 5 wt. %, or about 2 wt. % to about 4 wt. %, including ranges and subranges thereof, based on the total weight of the cosmetic composition. Further, the amount of thickener may be from 0.1, 0.2, 0.3, 0.4, 0.5, 0.6, 0.7, 0.8, 0.9, 1.0, or 1.5 wt. % to 2, 3, 4, 5, 6, 7, 8, 9, 10, 15, or 20 wt. %, including ranges and subranges thereof, based on the total weight of the cosmetic composition.

The thickener(s) may be chosen from xanthan gum, guar gum, biosaccharide gum, cellulose, acacia seneca gum, sclerotium gum, agarose, pechtin, gellan gum, hyaluronic acid. Additionally, the one or more thickeners may include polymeric thickeners selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some cases, the composition includes ammonium polyacryloyldimethyl taurate and/or sodium polyacrylate.

Many thickeners are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water. Non-limiting examples of various types of thickeners include:

Carboxylic Acid Polymers

These polymers are cross-linked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez® 10 (B.F. Goodrich) and copolymers of C1 0-30 alkyl acrylates with one or more monomers of acrylic acid, methacrylic acid, or one of their short chain (i.e., C1-4 alcohol) esters, wherein the cross-linking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

Crosslinked Polyacrylate Polymers

The cosmetic compositions can optionally contain cross-linked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078 4,599,379 and EP 228,868, which are all incorporated herein by reference in their entirety for all purposes.

Polyacrylamide Polymers

The cosmetic compositions can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The cosmetic composition may also contain thickening and texturising gels of the type as exemplified by the product range called Lubrajel® from United Guardian. These gels have moisturizing, viscosifying, stabilizing properties.

Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS11 from Michel Mercier Products Inc.

Gums

Other thickening and gelling agents useful herein include materials which are primarily derived from natural sources. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived from callus of plants belonging to Polyantes sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Active Ingredients

The cosmetic composition and/or the ceramide compositions may include one or more active ingredients. The cosmetic and/or ceramide composition may include 10 ppm to 10 wt. % (100,000 ppm), 10 ppm to 5 wt. % (50,000 ppm), 10 ppm to 2.5 wt. % (25,000 ppm), 10 ppm to 1 wt. % (10,000 ppm), 10 ppm to 0.5 wt. % (5,000 ppm), 10 ppm to 0.1 wt. % (1,000 ppm), or 10 ppm to 500 ppm of one or more active ingredients. In some cases, the one or more active ingredients is present in an amount from 10, 20, 30, 40, 50, 60, 70, 80, 90, 100, 150, or 200 ppm to 500, 600, 700, 800, 900, 0.1 wt. % (1000 ppm), 0.5 wt. % (5,000 ppm), 1 wt. % (10,000 ppm), 5 wt. % (50,000 ppm), or 10 wt. % (100,000 ppm), based on the total weight of the ceramide or cosmetic composition.

Non-limiting examples of the one or more active agents include adenosine, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, and a coenzyme. In some cases, the active ingredient is adenosine.

In one embodiment the formulation comprises an active ingredient such as a humectant and moisturizing ingredients, an anti-aging agent, a depigmenting agent, an anti-wrinkle agent, or an agent that treats oily skin.

Humectants and moisturizing ingredients may be included in the cosmetic composition and/or the ceramide compositions. For example, the active ingredient may include or be chosen from glycerol and its derivatives, urea and its derivatives, especially Hydrovance marketed by National Starch, lactic acid, hyaluronic acid, AHA, BHA, sodium pidolate, xylitol, serine, sodium lactate, ectoin and its derivatives, chitosan and its derivatives, collagen, plankton, an extract of Imperata cylindra sold under the name Moist 24 by Sederma, homopolymers of acrylic acid as Lipidure-HM of NOF Corporation, beta-glucan and in particular sodium carboxymethyl beta-glucan Mibelle-AG-Biochemistry, a mixture of oils passionflower, apricot, corn, and rice bran sold by Nestle under the name NutraLipids, a C-glycoside derivatives, in particular the C-13-D-xylopyranoside-2-hydroxypropane in the form of a solution at 30% by weight of active material in a water/propylene glycol mixture (60/40 wt %) as the product produced by the company Chimex under the trade name "Mexoryl SBB", a rose hip oil marketed by Nestle, a micro-algae extract Prophyridium cruentum enriched with zinc, marketed under the name by Vincience Algualane Zinc spheres of collagen and chondroitin sulfate of marine origin (Atelocollagen) sold by the company Engelhard Lyon under the name Marine Filling Spheres, hyaluronic acid spheres such as those marketed by Engelhard Lyon, and arginine.

Depigmenting agents include vitamin C and its derivatives and especially vitamin CG, CP and 3-O ethyl vitamin C, alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, ceramides and their counterparts, derived from plants such as chamomile, bearberry, the aloe family (vera, ferox, bardensis), mulberry, skullcap, a water kiwi fruit (Actinidia chinensis) marketed by Gattefosse, an extract of Paeonia suffruticosa root, such as that sold by Ichimaru Pharcos under the name Liquid Botanpi Be an extract of brown sugar (Saccharum officinarum) such as molasses extract marketed by Taiyo Kagaku under the name Liquid Molasses, without this list being exhaustive. Particular depigmenting agents include vitamin C and its derivatives and especially vitamin CG, CP and 3-0 ethyl vitamin C, alpha and beta arbutin, ferulic acid, kojic acid, resorcinol and derivatives, D pantheteine calcium sulfonate, lipoic acid, ellagic acid, vitamin BO, a water kiwi fruit (Actinidia chinensis) marketed by Gattefosse, an extract of Paeonia suffruticosa root, such as that sold by the company Ichimaru Pharcos under the name Botanpi Liquid B.

The term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Exemplary anti-wrinkle actives may be chosen from: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof.

Examples of such compounds are: adenosine and its derivatives and retinol and its derivatives such as retinol palmitate, ascorbic acid and its derivatives such as magnesium ascorbyl phosphate and ascorbyl glucoside; tocopherol and derivatives thereof such as tocopheryl acetate, nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxypropane as described in particular in EP-1345919, plant extracts including sea fennel and extracts of olive leaves, as well as plant and hydrolysates thereof such as rice protein hydrolysates or soybean proteins; algal extracts and in particular laminaria, bacterial extracts, the sapogenins such as diosgenin and extracts of Dioscorea plants, in particular wild yam, comprising: the a-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof.

As adenosine derivatives include especially non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside.

Other derivatives include adenosine receptor agonists such as adenosine adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxy-ethyl) phenethyl-amino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

In some instances, the cosmetic and/or ceramide composition comprises an active ingredient that addresses oily skin. These actives can be sebo-regulating or antiseborrhoeic agents capable of regulating the activity of sebaceous glands. These include: retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidonecarboxylate (or zinc pidolate), zinc lactate, zinc aspartate, zinc carboxylate, zinc salicylate 20, zinc cysteate; —derivatives particularly copper and copper pidolate as Cuivridone Solabia—extracts from plants of Arnica montana, Cinchona succirubra, Eugenia caryophyllata, Humulus lupulus, Hypericum perforatum, Mentha pipenta 25 Rosmarinus officinalis, Salvia officinalis and Thymus vulgaris, all marketed for example by Maruzen—extracts of meadowsweet (Spiraea ulmaria), such as that sold under the name Sebonormine by Silab—extracts of the alga Laminaria saccharina, such as that sold under the 30 name Phlorogine by Biotechmarine—the root extracts of burnet mixtures (Sanguisorba officinalis/Poterium officinale), rhizomes of ginger (Zingiber officinalis) and cinnamon bark (Cinnamomum cassia), such as that sold under the name Sebustop by Solabia—extracts of flaxseed such as that sold under the name Linumine by Lucas Meyer—Phellodendron extracts such as those sold under the name Phellodendron extract BG by Maruzen or Oubaku liquid B by Ichimaru Pharcos—of argan oil mixtures extract of Serenoa serrulata (saw palmetto) extract and sesame seeds such as that sold under the name Regu SEB by Pentapharm—mixtures of extracts of willowherb, of Terminalia chebula, nasturtium and of bioavailable zinc (microalgae), such as that sold under the name Seborilys Green Tech; —extracts of Pygeum afrianum such as that sold under the name Pygeum afrianum sterolic lipid extract by Euromed—extracts of Serenoa serrulata such as those sold under the name Viapure Sabal by Actives International, and those sold by the company Euromed—of extracts of plantain blends, Berberis aquifolium and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed laminaria extracts, such as that sold under the name Laminarghane by Biotechmarine—oligosaccharides seaweed Laminaria digitata, such as that sold under the name Phycosaccharide 30 AC by the company Codif—extracts of sugar cane such as that sold under the name Policosanol by the company Sabinsa, the sulfonated shale oil, such as that sold under the name Ichtyol Pale by Ichthyol—extracts of meadowsweet (Spiraea ulmaria) such as that sold under the name Cytobiol Ulmaire by societeLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of Sophora angustifolia, such as those sold under the name Sophora powder or Sophora extract by Bioland—extracts of cinchona bark succirubra such as that sold under the name Red Bark HS by Alban Muller—extracts of Quillaja saponaria such as that sold under the name 15 Panama wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20—phthalimidoperoxyhexanoic acid—citrate tri (C12-C13) sold under the name COSMACOL® ECI by Sasol; trialkyl citrate (C14-C15) sold under the name COSMACOL® ECL by Sasol—10-hydroxydecanoic acid, including mixtures acid-hydroxydecanoic October 25, sebacic acid and 1,10-decandiol such as that sold under the name Acnacidol BG by Vincience and mixtures thereof.

Methods of Producing Ceramide Containing Capsule

The instant disclosure also relates to methods for preparing the ceramide containing capsules and/or the ceramide compositions disclosed herein. An exemplary, non-limiting method for preparing a ceramide composition typically includes:

(I) providing a mixture at ambient temperature comprising:
  (a) an oily phase comprising:
    (i) ceramide NP,
    (ii) hydroxypalmitoyl sphinganine,
    (iii) 2-oleamido-1,3-octadecanediol, and
      wherein a weight ratio of the ceramide NP of (i) and the hydroxypalmitoyl sphinganine of (ii) to the 2-oleamido-1,3-octadecanediol of (iii) is from 1:2.5 to 1:5, and
    (iv) hydrophobic solvent,
  (b) a liposome precursor that is immiscible with water and with the oily phase, wherein the liposome precursor comprises:
    (i) a polycaprolactone,
    (ii) a block copolymer, and
    (iii) a surfactant,
  (c) acetone, wherein a weight ratio of the oily phase of (a) and the liposome precursor of (b) to the acetone of (c) is 1:20 to about 1:40,
(II) homogenizing the oily phase and the liposome precursor at a temperature of 30° C. or more;
(III) dispersing, the homogeneous mixture of (II) in a preheated aqueous phase, in order to obtain an emulsion, the preheated aqueous phase comprising a block copolymer;
(IV) distilling the solvent of (III) to remove acetone and concentrate from the mixture for the coacervation of the liposome precursor and for the coating of drops of the said oily phase by the coacervates to obtain a suspension;
(V) cooling the suspension of step (IV) to a temperature for the formation of capsules by the precipitation and/or crystallization of the coacervates; and
(VI) adding hydroxyacetophenone.

The mixture typically includes a weight ratio of the combination of oily phase of (a) and the liposome precursor of (b) to the acetone of (c) is 1:20 to about 1:40. In some instances, however, the weight ratio of the oily phase of (a) and liposome precursor of (b) to the acetone of (c) is 1:20 to 1:40, 1:25 to 1:40, 1:27 to 1:40, 1:20 to 1:35, 1:25 to 1:33, or 1:27 to 1:33, including ranges and subranges therebetween. In yet a further embodiment, the weight ratio of the oily phase of (a) and liposome precursor of (b) to the acetone of (c) may be about 1:30.

The homogenization of the oily phase and the liposome precursor occurs at a temperature greater than room temperature. For example, the homogenization of step (II) typically occurs at a temperature of 30° C. or more, preferably about 40° C. or more, about 45° C. or more, or about 50° C. or more. Additionally, it may be desirable to homogenize the oily phase and the liposome precursor at a temperature that does not exceed 100° C., e.g., does not exceed 80° C. and/or 60° C. In at least one instance, the homogenization of step (II) occurs at a temperature of about 50° C.

Additional subject matter relating to steps (I)-(VI) or methods for producing capsules may be found in US Patent Publication no. 2009/0047341, which is incorporated herein in its entirety for all purposes. One of ordinary skill in the art would understand how to implement the methods for producing the ceramide containing capsules and/or the ceramide compositions based on the incorporated references and disclosure herein.

Methods of Use

In accordance with an aspect of the disclosure, provided are methods for preparing cosmetic compositions from the ceramide compositions and/or the ceramide containing capsule. Advantageously, cosmetic compositions having ceramide containing capsules may be prepared by adding the ceramide compositions during or after the procedures for preparing the cosmetic compositions.

According to another aspect of the instant disclosure, methods are provided for using the cosmetic compositions described herein. For example, the cosmetic compositions can be used in a method for supporting natural lipid barrier function of skin, wherein the method comprises applying the cosmetic composition to skin or hair. The methods may also improve the skin barrier functionality of a user's skin. In some instances, the methods may promote regeneration, renewal, and/or repair of compromised skin. Additionally or alternatively, the methods may provide improved skin appearance, such as anti-inflammation, improved skin pigmentation, etc.

Typically, the cosmetic compositions are applied to the skin or hair of humans. In some cases, the composition is applied to the face. Furthermore, the cosmetic composition can be used in methods for treating dryness of the skin and/or hair, repairing damage to skin and/or hair (for example, damage associated with ageing, UV exposure, dryness, etc.), and for diminishing the appearance of wrinkles, dark spots, and uneven skin texture of skin. These methods also entail application of the cosmetic compositions described herein to the skin and/or hair, and in some cases to the face. The aforementioned methods are typically non-therapeutic.

The cosmetic composition may be applied once per day, twice per day, or more than once or twice per day. In some cases, the cosmetic composition is applied in the evenings before bed. In other cases, the cosmetic compositions are applied in the morning. In still other cases, the composition may be applied immediately after washing the skin and/or hair. The compositions may be used once, or for a series of days, weeks, or months. For example, the compositions may be used daily for a period of 1, 2, 3, 4, 5, 6, 7, 8 or more weeks, or months.

Embodiments of the Disclosure

In certain embodiments, the ceramide compositions of the instant disclosure include:
(I) capsules dispersed in the ceramide composition, the capsules comprising:
 (a) a shell comprising:
  (i) a polycaprolactone, such as about 10 to about 70 wt. %, based on the total weight of the components of the shell, of a polycaprolactone selected from polycaprolactone diols having a weight average molecular weight from 100 to 20,000 and/or up to 100 monomer units,
  (ii) a block copolymer, e.g., about 10 to about 70 wt. %, based on the total weight of the components of the shell, of a poloxamer having a weight average molecular weight from 1,000 to 900,000, and
  (iii) a surfactant, such as about 10 to about 70 wt. %, based on the total weight of the components of the shell, of a surfactant chosen from phospholipid surfactants, and
 (b) a core comprising:
  (i) ceramide NP, e.g., in an amount ranging from about 1 to about 15 wt. %, based on the total weight of the components of the core,
  (ii) hydroxypalmitoyl sphinganine, e.g., in an amount ranging from about 1 to about 15 wt. %, based on the total weight of the components of the core,
  (iii) 2-oleamido-1,3-octadecanediol, e.g., in an amount ranging from about 1 to about 60 wt. %, based on the total weight of the components of the core,
   wherein a weight ratio of the ceramide NP of (i) and the hydroxypalmitoyl sphinganine of (ii) to the 2-oleamido-1,3-octadecanediol of (iii) is from 1:2.5 to 1:5 or from 1:2.5 to
  (iv) hydrophobic solvent, such as a 2-octyl-1-dodecanol, e.g., in an amount ranging from about 35 to about 90 wt. %, based on the total weight of the components of the core;
(II) hydrophilic solvent, such as water; and
(III) hydroxyacetophenone.

In additional embodiments, a method for preparing a ceramide composition includes:
(I) providing a mixture at ambient temperature comprising:
 (a) an oily phase comprising:
  (i) ceramide NP,
  (ii) hydroxypalmitoyl sphinganine,
  (iii) 2-oleamido-1,3-octadecanediol,
   wherein a weight ratio of the ceramide NP of (i) and the hydroxypalmitoyl sphinganine of (ii) to the 2-oleamido-1,3-octadecanediol of (iii) is from 1:2.5 to 1:5 or from 1:2.5 to 1:4, and
  (iv) hydrophobic solvent, such as a 2-octyl-1-dodecanol;
 (b) a liposome precursor that is immiscible with water and with the oily phase, wherein the liposome precursor comprises:
  (i) a polycaprolactone, such as a polycaprolactone selected from polycaprolactone diols having a weight average molecular weight from 100 to 20,000 and/or up to 100 monomer units,
(ii) a block copolymer, such as a poloxamer having a weight average molecular weight from 1,000 to 900,000, and
(iii) a surfactant, such as those chosen from phospholipid surfactants, and
(c) acetone, wherein a weight ratio of the oily phase of (a) and the liposome precursor of (b) to the acetone of (c) is 1:20 to about 1:40,
(II) homogenizing the oily phase and the liposome precursor at a temperature of 30° C. or more;
(III) dispersing, the homogeneous mixture of (II) in a preheated aqueous phase, in order to obtain an emulsion, the preheated aqueous phase comprising a block copolymer;
(IV) distilling the solvent of (III) to remove acetone and concentrate from the mixture for the coacervation of the liposome precursor and for the coating of drops of the said oily phase by the coacervates to obtain a suspension;
(V) cooling the suspension of step (IV) to a temperature for the formation of capsules by the precipitation and/or crystallization of the coacervates; and
(VI) adding hydroxyacetophenone.

In a further embodiment, provided is a cosmetic composition including:
(A) about 1% to about 20 wt. % of a ceramide composition, the ceramide composition comprising:
(I) capsules dispersed in the ceramide composition, the capsules comprising:
(a) a shell comprising:
(i) a polycaprolactone, such as about 10 to about 70 wt. %, based on the total weight of the components of the shell, of a polycaprolactone selected from polycaprolactone diols having a weight average molecular weight from 400 to 10,000 and/or up to 100 monomer units,
(ii) a poloxamer, e.g., about 10 to about 70 wt. %, based on the total weight of the components of the shell, of a poloxamer having a weight average molecular weight from 1,000 to 800,000, and, and
(iii) a surfactant comprising a phospholipid group, such as lecithin in an amount of about 10 to about 70 wt. %, based on the total weight of the components of the shell, and
(b) a core comprising:
(i) ceramide NP, e.g., in an amount ranging from about 1 to about 15 wt. %, based on the total weight of the components of the core,
(ii) hydroxypalmitoyl sphinganine, e.g., in an amount ranging from about 1 to about 15 wt. %, based on the total weight of the components of the core,
(iii) 2-oleamido-1,3-octadecanediol, e.g., in an amount ranging from about 1 to about 60 wt. %, based on the total weight of the components of the core,
wherein a weight ratio of the ceramide NP of (i) and the hydroxypalmitoyl sphinganine of (ii) to the 2-oleamido-1,3-octadecanediol of (iii) is from 1:2.5 to 1:5 or from 1:2.5 to 1:4, and
(iv) hydrophobic solvent, such as a 2-octyl-1-dodecanol, e.g., in an amount ranging from about 35 to about 90 wt. %, based on the total weight of the components of the core;
(II) hydrophilic solvent, such as water; and
(III) hydroxyacetophenone;
(B) optionally, an emulsifier, such as those selected from amphoteric, anionic, cationic or nonionic emulsifiers in amount ranging from about 0.001 to about 25 wt. %, based on the total weight of the cosmetic composition;
(C) optionally, a polyol, including polyols having from 2 to 15 carbon atoms and at least two hydroxyl groups in amount ranging from about 0.1 to about 25 wt. %, based on the total weight of the cosmetic composition;
(D) optionally, a fatty compound, such as those selected from oils, mineral oil, fatty alcohols, fatty acids, fatty alcohol derivatives, and fatty acid derivatives in an amount ranging about 0.1 to about 25 wt. %, based on the total weight of the cosmetic composition; and
(E) optionally, a monoalcohol.

EXAMPLES

Implementation of the present disclosure is provided by way of the following examples. The following examples serve to elucidate aspects of the technology without being limiting in nature.

Example 1

Formulations

An example of ceramide compositions (Example 1) was prepared. Four comparative examples of ceramide compositions (Comparative Examples 1-4) were prepared in accordance with the method for preparing Example 1. The formulations for Example 1 and Comparative Examples 1-4 are provided in Table 1, below.

TABLE 1

| | | INCI | Ex. 1 | Comp. 1 | Comp. 2 | Comp. 3 | Comp. 4 |
|---|---|---|---|---|---|---|---|
| Shell | Poloxamer | POLOXAMER 188 | 0.5 | 0.5 | 0.5 | 0.5 | 0.5 |
| | Polycaprolactone | POLYCAPROLACTONE DIOL | 1 | 1 | 1 | 1 | 1 |
| | Liposome Precursor | LECITHIN | 1 | 1 | 1 | 1 | 1 |
| Core | Ceramide | (i) CERAMIDE III NP | 0.2 | 0.25 | 0.25 | 0.25 | 0.2 |
| | | (ii) CERAMIDE 5 - HYDROXYPALMITOYL SPHINGANINE | 0.2 | 0.25 | 0.25 | 0.25 | 0.2 |
| | | (iii) N-OLEYL DI-HYDROSPHINGOSINE TECHNIQUE ( 2-OLEAMIDO-1,3-OCTADECANEDIOL) | 1.1 | 1 | 1 | 1 | 1.1 |

TABLE 1-continued

| | INCI | Ex. 1 | Comp. 1 | Comp. 2 | Comp. 3 | Comp. 4 |
|---|---|---|---|---|---|---|
| weight ratio of (i) to (ii) to (iii) | | 1:1:5.5 | 1:1:4 | 1:1:4 | 1:1:4 | 1:1:5.5 |
| Fatty Alcohol | 2-OCTYL-1-DODECANOL | 3.5 | 3.5 | 3.5 | 3.5 | 3.5 |
| Preservatives | PHENYLETHYL ALCOHOL | | 1 | | | |
| | PHENOXY ETHANOL | | 0.7 | | | |
| | 4'-HYDROXYACETOPHENONE | 1 | | 1 | | |
| | PENTANE-1,2-DIOL | | | | 10 | 10 |
| Water | WATER | 91.5 | 90.8 | 91.5 | 82.5 | 82.5 |

Example 2

Stability Evaluation

Example 1 and Comparative Examples 1-4 were evaluated for temporal stability. Specifically, samples of Example 1 and Comparative Examples 1-4 were kept in environmental chambers at temperatures of standard room temperature, 5° C., and 45° C. The samples were then evaluated after one week.

Example 1 was determined to be stable and did not exhibit clotting/aggregation. Specifically, Example 1 was determined to not exhibit clotting because Example 1 had a uniform milky liquid, white to pinky appearance. Comparative Example 1 also did not exhibit clotting. Comparative Example 2 exhibited slight clotting. In particular, Comparative Example 2 exhibited slight clotting by forming clumps and having a non-uniform appearance. Comparative Example 3 exhibited clotting. In particular, Comparative Example 3 was designated as exhibiting clotting because Comparative Example 3 separated to form a significant amount of clumps and a liquid medium. Comparative Example 4 was determined to be unstable as Comparative Example 4 formed a thick paste.

Example 3

Evaluation Ceramide Weight Ratios

Three compositions (Compositions A-C) containing different ratios of ceramides were prepared and evaluated. The formulation of the three compositions are provided in Table 2, below.

TABLE 2

| | INCI | Composition A | Composition B | Composition C |
|---|---|---|---|---|
| (i) | CERAMIDE III NP | 0.25 | 0.2 | 0.15 |
| (ii) | CERAMIDE 5 - HYDROXYPALMITOYL SPHINGANINE | 0.25 | 0.2 | 0.15 |
| (iii) | N-OLEYL DI-HYDROSPHINGOSINE TECHNIQUE (2-OLEAMIDO-1,3-OCTADECANEDIOL) | 1 | 1.1 | 1.2 |
| weight ratio of (i) to (ii) to (iii) | | 1:1:4 | 1:1:5.5 | 1:1:8 |

Compositions A-C were prepared in a beaker by heating the three ceramides to 50° C. in 2-octyl-1-dodecanol in the amounts and ratios provided in Table 2. Compositions A-C were visually clear and transparent at a temperature of 50° C. After Compositions A-C were cooled to room temperature, Composition A was visually determined to be slightly cloudy, while Compositions B and C were clear and transparent. The solubility of Compositions B and C was better than the solubility of Composition A.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the hair cleansing compositions of the instant disclosure can be free or essentially free of all components and elements positively recited throughout the instant disclosure.

In some instances, the hair cleansing compositions of the present disclosure may be substantially free of non-incidental amounts of the ingredient(s) or compound(s) described herein. A non-incidental amount of an ingredient or compound is the amount of that ingredient or compound that is added into the hair cleansing composition by itself. For example, a hair cleansing composition may be substantially free of a non-incidental amount of an ingredient or compound, although such ingredient(s) or compound(s) may be present as part of a raw material that is included as a blend of two or more compounds.

Some of the various categories of components identified may overlap. In such cases where overlap may exist and the hair cleansing composition includes both components (or the composition includes more than two components that overlap), an overlapping compound does not represent more than one component. For example, certain compounds may be characterized as both an emulsifier and a surfactant. If a particular hair composition includes both an emulsifier and a surfactant, the compounds that may be characterized as both an emulsifier and a surfactant will serve only as either the emulsifier or the surfactant—not both.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

The term "treat" (and its grammatical variations) as used herein refers to the application of the compositions of the present disclosure onto the surface of keratinous substrates such as hair on a user's head and/or body.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of silicones.

What is claimed is:

1. A ceramide composition comprising:
   (I) capsules dispersed in the ceramide composition, the capsules comprising:
      (a) a shell comprising:
         (i) a polycaprolactone,
         (ii) a block copolymer, and
         (iii) a surfactant, and
      (b) a core comprising:
         (i) ceramide NP,
         (ii) hydroxypalmitoyl sphinganine,
         (iii) 2-oleamido-1,3-octadecanediol,
            wherein a weight ratio of the ceramide NP of (i) and the hydroxypalmitoyl sphinganine of (ii) to the 2-oleamido-1,3-octadecanediol of (iii) is from 1:2.5 to 1:5, and
         (iv) hydrophobic solvent;
   (II) hydrophilic solvent; and
   (III) hydroxyacetophenone.

2. The ceramide composition of claim 1, wherein the weight ratio of the ceramide NP of (i) and the hydroxypalmitoyl sphinganine of (ii) to the 2-oleamido-1,3-octadecanediol of (iii) is from 1:2.5 to 1:4.

3. The ceramide composition of claim 1, wherein the capsules have an average diameter of about 200 nm to about 400 nm.

4. The ceramide composition of claim 1, wherein the surfactant comprises a phospholipid group.

5. The ceramide composition of claim 1, wherein the hydrophobic solvent comprises a fatty alcohol.

6. The ceramide composition of claim 5, wherein the fatty alcohol is selected from cetearyl alcohol, cetyl alcohol, stearyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, octyldodecanol, 2-octyl-1-dodecanol, and a mixture thereof.

7. The ceramide composition of claim 5, wherein the fatty alcohol is 2-octyl-1-dodecanol.

8. The ceramide composition of claim 1, wherein the hydrophilic solvent comprises water.

9. The ceramide composition of claim 1, wherein the core further comprises a ceramide or derivative thereof selected from at least one ceramide and/or a derivative thereof selected from ceramide-EOS, ceramide-NS, ceramide-EOH, ceramide-AS, ceramide-NH, ceramide-AP, ceramide-AH, Ceramide-OS, ceramide-OH, and a mixture thereof.

10. The ceramide composition of claim 1, wherein the core comprises:
   (i) about 2 to about 8 wt. % of ceramide NP,
   (ii) about 2 to about 8 wt. % of hydroxypalmitoyl sphinganine,
   (iii) about 10 to about 40 wt. % of 2-oleamido-1,3-octadecanediol, and
   (iv) about 44 to about 86 wt. % of hydrophobic solvent, wherein the foregoing weight percentages of (i)-(iv) are based on the total weight of the core of (b).

11. The ceramide composition of claim 1 being free of phenoxyethanol.

12. The ceramide composition of claim 1 being free of penylethylalcohol.

13. The ceramide composition of claim 1 further comprising at least one of:
   (IV) an emulsifier;
   (V) a polyol;
   (VI) a fatty compound; and
   (VII) a monoalcohol.

14. A method of improving the appearance of skin comprising:
   applying the ceramide composition of claim 1 to skin for improving the appearance of skin.

15. A method for preparing a ceramide composition comprising:
   (I) providing a mixture at ambient temperature comprising:
      (a) an oily phase comprising:
         (i) ceramide NP,
         (ii) hydroxypalmitoyl sphinganine,
         (iii) 2-oleamido-1,3-octadecanediol, and
            wherein a weight ratio of the ceramide NP of (i) and the hydroxypalmitoyl sphinganine of (ii) to the 2-oleamido-1,3-octadecanediol of (iii) is from 1:2.5 to 1:5, and
         (iv) hydrophobic solvent,
      (b) a liposome precursor that is immiscible with water and with the oily phase, wherein the liposome precursor comprises:
         (i) a polycaprolactone, and
         (ii) a surfactant,
      (c) acetone, wherein a weight ratio of the oily phase of (a) and the liposome precursor of (b) to the acetone of (c) is 1:20 to about 1:40,
   (II) homogenizing the oily phase and the liposome precursor at a temperature of 30° C. or more;
   (III) dispersing, the homogeneous mixture of (II) in a preheated aqueous phase, in order to obtain an emulsion, the preheated aqueous phase comprising a block copolymer;

(IV) distilling the solvent of (III) to remove acetone and concentrate from the mixture for the coacervation of the liposome precursor and for the coating of drops of the said oily phase by the coacervates to obtain a suspension;

(V) cooling the suspension of step (IV) to a temperature for the formation of capsules by the precipitation and/or crystallization of the coacervates; and (VI) adding hydroxyacetophenone.

16. The method of claim 15, wherein the polycaprolactone has a weight average molecular weight of about 400 to about 10,000.

17. The method of claim 15, wherein the polycaprolactone comprises up to 100 monomer units.

18. The method of claim 15, wherein the weight ratio of the ceramide NP of (i) and the hydroxypalmitoyl sphinganine of (ii) to the 2-oleamido-1,3-octadecanediol of (iii) is from 1:2.5 to 1:4.

19. A cosmetic composition comprising:
    (A) about 1% to about 20 wt. % of a ceramide composition, the ceramide composition comprising:
        (I) capsules dispersed in the ceramide composition, the capsules comprising:
            (a) a shell comprising:
                (i) a polycaprolactone,
                (ii) a poloxamer, and
                (iii) a surfactant comprising a phospholipid group, and
            (b) a core comprising:
                (i) ceramide NP,
                (ii) hydroxypalmitoyl sphinganine,
                (iii) 2-oleamido-1,3-octadecanediol,
                    wherein a weight ratio of the ceramide NP of (i) and the hydroxypalmitoyl sphinganine of (ii) to the 2-oleamido-1,3-octadecanediol of (iii) is from 1:2.5 to 1:5, and
                (iv) hydrophobic solvent,
        (II) hydrophilic solvent, and
        (III) hydroxyacetophenone;
    (B) optionally, an emulsifier;
    (C) optionally, a polyol;
    (D) optionally, a fatty compound; and
    (E) optionally, a monoalcohol.

20. The cosmetic composition of claim 19, wherein the cosmetic composition improves skin barrier function.

\* \* \* \* \*